United States Patent
Irisawa

(10) Patent No.: US 12,419,522 B2
(45) Date of Patent: *Sep. 23, 2025

(54) INSERT, PHOTOACOUSTIC MEASUREMENT DEVICE COMPRISING INSERT, AND METHOD FOR MANUFACTURING INSERT

(71) Applicant: FUJIFILM Corporation, Tokyo (JP)

(72) Inventor: Kaku Irisawa, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 200 days.

This patent is subject to a terminal disclaimer.

(21) Appl. No.: 18/341,533

(22) Filed: Jun. 26, 2023

(65) Prior Publication Data

US 2023/0355102 A1    Nov. 9, 2023

Related U.S. Application Data

(60) Division of application No. 16/353,300, filed on Mar. 14, 2019, now Pat. No. 11,766,178, which is a
(Continued)

(30) Foreign Application Priority Data

Sep. 27, 2016  (JP) ................. 2016-187841

(51) Int. Cl.
*A61B 5/00* (2006.01)
*A61B 5/06* (2006.01)
(Continued)

(52) U.S. Cl.
CPC ............ *A61B 5/0095* (2013.01); *A61B 5/061* (2013.01); *A61B 5/6848* (2013.01);
(Continued)

(58) Field of Classification Search
CPC ..... A61B 5/0095; A61B 5/061; A61B 5/6848; A61B 8/0841; A61B 8/4416;
(Continued)

(56) References Cited

U.S. PATENT DOCUMENTS

| 4,846,546 A | 7/1989 | Cuda |
| 5,048,530 A | 9/1991 | Hurwitz |

(Continued)

FOREIGN PATENT DOCUMENTS

| JP | 2015-231583 A | 12/2015 |
| WO | WO 2014/109148 A1 | 7/2014 |

OTHER PUBLICATIONS

European Communication purs int to Article 94(3) EPC for European Application No. 17855762.5. dated Nov. 28, 2024.
(Continued)

*Primary Examiner* — John D Li
(74) *Attorney, Agent, or Firm* — Birch, Stewart, Kolasch & Birch, LLP

(57) ABSTRACT

An insert includes: a puncture needle main body which has an opening at a tip and is formed in a hollow shape and of which at least a tip portion is inserted into a subject; an optical fiber that is provided in a hollow portion of the puncture needle main body along a length direction of the puncture needle main body; and a photoacoustic wave generation unit that is provided at a light emission end of the optical fiber which is disposed on a tip side of the puncture needle main body, absorbs light emitted from the light emission end, and generates photoacoustic waves. A through-hole is formed in a wall portion forming the hollow portion and the photoacoustic wave generation unit is fixed to the through-hole.

19 Claims, 10 Drawing Sheets

Related U.S. Application Data continuation of application No. PCT/JP2017/033345, filed on Sep. 14, 2017.

(51) Int. Cl.

| | | |
|---|---|---|
| *A61B 8/00* | (2006.01) | |
| *A61B 8/08* | (2006.01) | |
| *A61B 17/34* | (2006.01) | |
| *A61B 90/00* | (2016.01) | |
| *G01N 29/24* | (2006.01) | |

(52) U.S. Cl.
CPC .......... *A61B 8/0841* (2013.01); *A61B 8/4416* (2013.01); *G01N 29/2418* (2013.01); *A61B 2017/3413* (2013.01); *A61B 2090/373* (2016.02); *A61B 2090/378* (2016.02); *A61B 2090/3945* (2016.02)

(58) Field of Classification Search
CPC ...... A61B 2090/373; A61B 2017/3413; G01N 29/2418
See application file for complete search history.

(56) References Cited

U.S. PATENT DOCUMENTS

| | | |
|---|---|---|
| 2005/0175347 A1 | 8/2005 | Ray et al. |
| 2008/0051655 A1 | 2/2008 | Sato et al. |
| 2010/0289664 A1 | 11/2010 | Mizushima et al. |
| 2014/0180056 A1 | 6/2014 | Hoseit |
| 2014/0180087 A1* | 6/2014 | Millett ............... A61B 5/02158 600/437 |
| 2015/0119681 A1 | 4/2015 | Song et al. |
| 2015/0123667 A1 | 5/2015 | Solarz |
| 2015/0297092 A1 | 10/2015 | Irisawa |
| 2016/0137839 A1 | 5/2016 | Rolland et al. |
| 2016/0287085 A1 | 10/2016 | Fukui et al. |
| 2017/0023740 A1 | 1/2017 | Kewitsch |
| 2017/0209119 A1 | 7/2017 | Masaki et al. |

OTHER PUBLICATIONS

European Communication pursuant to Article 94(3) EPC for European Application No. 17855762.5, dated Jun. 27, 2022.
Extended European Search Report, dated Aug. 13, 2019, for European Application No. 17855762.5.
International Preliminary Report on Patentability and Written Opinion of the International Searching Authority for International Application No. PCT/JP2017/033345, dated Apr. 11, 2019, with English translation.
International Search Report for International Application No. PCT/JP2017/033345, dated Nov. 21, 2017, with English translation.
Japanese Office Action, dated Oct. 15, 2019, for Japanese Application No. 2018-542382, along with an English translation.
Lötters et al., "Polydimethylsiloxane, a photocurable rubberelastic polymer used as spring material in micromechanical sensors", Microsystem Technologies, 1997, pp. 64-67(4 pages).

\* cited by examiner

FIG. 11
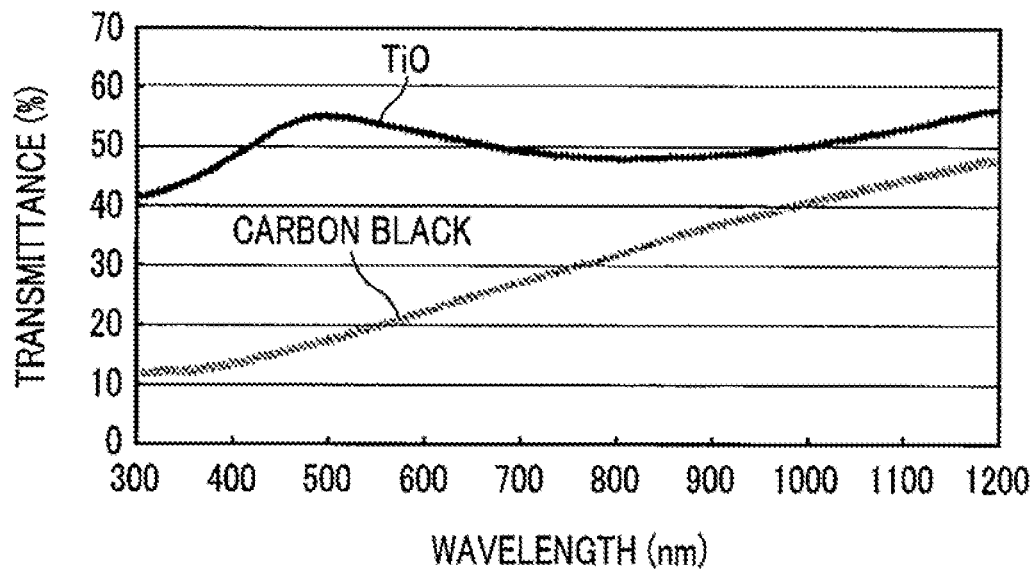
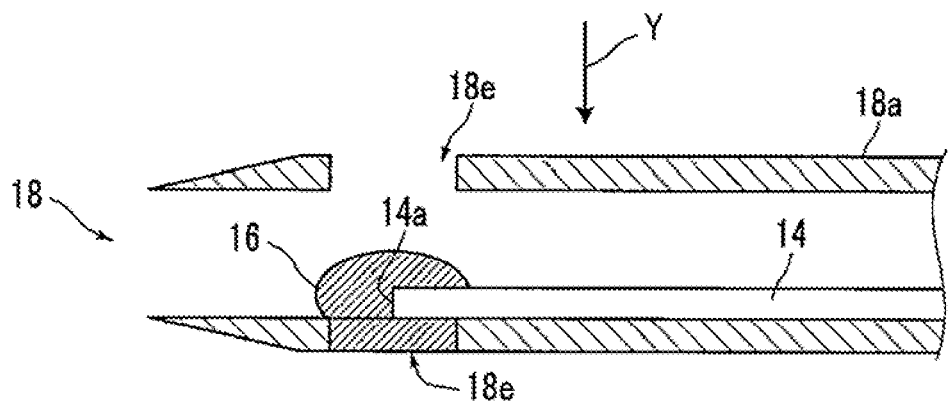
FIG. 12A
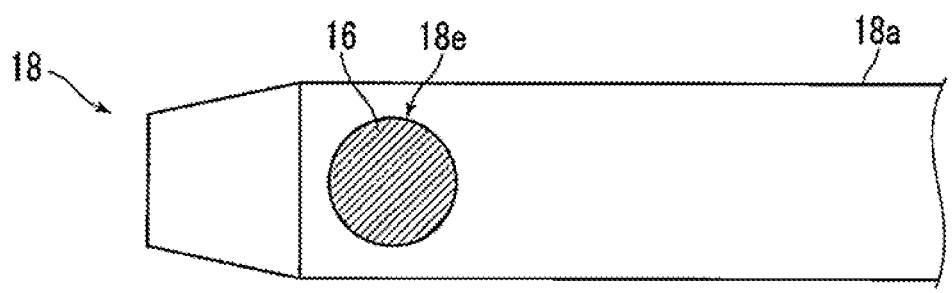
FIG. 12B

INSERT, PHOTOACOUSTIC MEASUREMENT DEVICE COMPRISING INSERT, AND METHOD FOR MANUFACTURING INSERT

CROSS-REFERENCE TO RELATED APPLICATIONS

This application is a Divisional of copending application Ser. No. 16/353,300, filed on Mar. 14, 2019, which is the National Phase under 35 U.S.C. § 371 of International Application No. PCT/JP2017/033345, filed on Sep. 14, 2017, which claims the benefit under 35 U.S.C. § 119(a) to Patent Application No. 2016-187841, filed in Japan on Sep. 27, 2016, all of which are hereby expressly incorporated by reference into the present application.

BACKGROUND

1. Technical Field

The present invention relates to an insert which comprises a photoacoustic wave generation portion that absorbs light and generates photoacoustic waves and of which at least a portion is inserted into a subject, a photoacoustic measurement device comprising the insert, and a method for manufacturing the insert.

2. Related Art

An ultrasonography method has been known as a kind of image inspection method that can non-invasively inspect the internal state of a living body. In ultrasonography, an ultrasound probe that can transmit and receive ultrasonic waves is used. In a case in which the ultrasound probe transmits ultrasonic waves to a subject (living body), the ultrasonic waves travel in the living body and are reflected from the interface between tissues. The ultrasound probe receives the reflected ultrasonic waves and a distance is calculated on the basis of the time until the reflected ultrasonic waves return to the ultrasound probe. In this way, it is possible to capture an image indicating the internal aspect of the living body.

In addition, photoacoustic imaging has been known which captures the image of the inside of a living body using a photoacoustic effect. In general, in the photoacoustic imaging, the inside of the living body is irradiated with pulsed laser light. In the inside of the living body, a living body tissue absorbs the energy of the pulsed laser light and ultrasonic waves (photoacoustic waves) are generated by adiabatic expansion caused by the energy. For example, an ultrasound probe detects the photoacoustic waves and a photoacoustic image is formed on the basis of a detection signal. In this way, it is possible to visualize the inside of the living body on the basis of the photoacoustic waves.

In addition, as a technique related to the photoacoustic imaging, JP2015-231583A discloses a puncture needle in which a photoacoustic wave generation portion that absorbs light and generates photoacoustic waves is provided in the vicinity of a tip. In the puncture needle, an optical fiber is provided up to the tip of the puncture needle and light guided by the optical fiber is emitted to the photoacoustic wave generation portion. An ultrasound probe detects the photoacoustic waves generated by the photoacoustic wave generation portion and a photoacoustic image is generated on the basis of a detection signal of the photoacoustic waves. In the photoacoustic image, a part of the photoacoustic wave generation portion appears as a bight point, which makes it possible to check the position of the puncture needle using the photoacoustic image.

SUMMARY

Here, for example, in a case in which photoacoustic imaging is performed using the puncture needle disclosed in JP2015-231583A, the photoacoustic waves generated from the photoacoustic wave generation portion are mainly emitted through an opening formed in the tip of the puncture needle.

For example, in an operation such as blood vessel needling, the opening in the tip of the puncture needle faces a blood vessel. Therefore, in a case in which the puncture needle is inserted without an opening side surface of the puncture needle facing the ultrasound probe, photoacoustic waves are reflected from an internal metal surface of the puncture needle which is opposite to the opening side of the puncture needle. As a result, the signal intensity of the photoacoustic waves detected by the ultrasound probe is low and the visibility of the tip of the puncture needle is low.

In addition, the photoacoustic waves which have been reflected from the inner metal surface of the puncture needle and then have traveled in a direction different from the direction of the ultrasound probe are likely to cause a strong artifact at an unintended position.

The invention has been made in view of the above-mentioned problems and an object of the invention is to provide an insert that can detect a tip of the insert, such as a puncture needle, with high sensitivity, a photoacoustic measurement device comprising the insert, and a method for manufacturing the insert.

According to the invention, there is provided an insert comprising: an insert main body which has an opening at a tip and is formed in a hollow shape and of which at least a tip portion is inserted into a subject; a light guide member that is provided in a hollow portion of the insert main body along a length direction of the insert main body; and a photoacoustic wave generation unit that is provided at a light emission end of the light guide member which is disposed on a tip side of the insert main body, absorbs light emitted from the light emission end, and generates photoacoustic waves. A through-hole is formed in a wall portion forming the hollow portion and the photoacoustic wave generation unit is fixed to the through-hole.

In the insert according to the invention, the through-hole may have a shape in which the through-hole extends in the length direction of the insert main body rather than in a direction perpendicular to the length direction.

In the insert according to the invention, the through-hole may be filled with the same material as that forming the photoacoustic wave generation unit and the photoacoustic wave generation unit and a tip portion of the light guide member may be fixed to the wall portion.

In the insert according to the invention, the photoacoustic wave generation unit may be fixed to the through-hole by a resin and the through-hole may be filled with the resin.

In the insert according to the invention, preferably, the resin is a photocurable resin.

In the insert according to the invention, preferably, the photocurable resin is a resin that is cured by visible light or ultraviolet light.

In the insert according to the invention, the photoacoustic wave generation unit may be made of a black resin.

In the insert according to the invention, the photoacoustic wave generation unit may be made of a material that transmits visible light.

In the insert according to the invention, the photoacoustic wave generation unit may be made of a material that transmits visible light and absorbs near-infrared light.

In the insert according to the invention, the photoacoustic wave generation unit may be made of a material including a pigment that transmits visible light and absorbs near-infrared light and a photocurable resin.

In the insert according to the invention, preferably, the light guide member is an optical fiber.

In the insert according to the invention, preferably, the insert main body is a needle that is inserted into the subject.

According to the invention, there is provided a photoacoustic measurement device comprising: the insert according to the invention; a light source unit that emits light which is absorbed by the photoacoustic wave generation unit of the insert; and an acoustic wave detection unit that detects photoacoustic waves generated from the photoacoustic wave generation unit after at least a portion of the insert is inserted into the subject.

In the photoacoustic measurement device according to the invention, the photoacoustic wave generation unit may be made of a material that transmits visible light and the light source unit may comprise a first light source that emits the light which is absorbed by the photoacoustic wave generation unit and a second light source that emits the visible light.

In the photoacoustic measurement device according to the invention, the first light source may emit near-infrared light.

In the photoacoustic measurement device according to the invention, the second light source may emit the visible light from a surface of a housing of the light source unit to the outside.

In the photoacoustic measurement device according to the invention, the light source unit may comprise optical members that make the light emitted from the first light source and the visible light emitted from the second light source incident on the light guide member of the insert.

In the photoacoustic measurement device according to the invention, the optical members may include a multiplexing prism.

In the photoacoustic measurement device according to the invention, the optical members may include a fiber combiner.

In the photoacoustic measurement device according to the invention, the optical members may include a condensing lens that condenses both the light emitted from the first light source and the light emitted from the second light source.

In the photoacoustic measurement device according to the invention, the optical members may include a first optical fiber that guides the light emitted from the first light source and a second optical fiber that guides the light emitted from the second light source and the photoacoustic measurement device may comprise a fiber switching unit that switches a position of a light emission end of the first optical fiber and a position of a light emission end of the second optical fiber between a first position where light emitted from the first optical fiber is incident on the light guide member and a second position where light emitted from the second optical fiber is incident on the light guide member.

According to the invention, there is provided a first method for manufacturing the insert. The first method comprises: inserting the light guide member into the hollow portion of the insert such that the light emission end of the light guide member is disposed on the through-hole; filling the through-hole with a material forming the photoacoustic wave generation unit while supplying the material to the light emission end of the light guide member; and curing the material after the filling.

According to the invention, there is provided a second method for manufacturing the insert in which the photoacoustic wave generation unit is made of a material that transmits light guided by the light guide member. The second method comprises: forming the photoacoustic wave generation unit at the light emission end of the light guide member; inserting the light guide member provided with the photoacoustic wave generation unit into the hollow portion of the insert such that the photoacoustic wave generation unit is disposed on the through-hole; filling the through-hole with a photocurable resin while supplying the photocurable resin to the photoacoustic wave generation unit; and irradiating the photocurable resin with the light guided by the light guide member to cure the photocurable resin.

According to the invention, there is provided a third method for manufacturing the insert in which the photoacoustic wave generation unit is made of a material including a photocurable resin that is cured by light guided by the light guide member. The third method comprises: inserting the light guide member into the hollow portion of the insert such that the light emission end of the light guide member is disposed on the through-hole; filling the through-hole with the material including the photocurable resin while supplying the material to the light emission end of the light guide member; and irradiating the photocurable resin with the light guided by the light guide member to cure the photocurable resin.

The insert according to the invention comprises: an insert main body which has an opening at a tip and is formed in a hollow shape and of which at least a tip portion is inserted into a subject; a light guide member that is provided in a hollow portion of the insert main body along a length direction of the insert main body; and a photoacoustic wave generation unit that is provided at a light emission end of the light guide member which is disposed on a tip side of the insert main body, absorbs light emitted from the light emission end, and generates photoacoustic waves. A through-hole is formed in a wall portion forming the hollow portion and the photoacoustic wave generation unit is fixed to the through-hole. Therefore, it is possible to detect the tip of the insert with high sensitivity.

BRIEF DESCRIPTION OF THE DRAWINGS

Exemplary embodiments according to the technique of the present disclosure will be described in detail based on the following figures, wherein:

FIG. 11 is a diagram illustrating the light transmission characteristics of TiO and carbon black;

FIGS. 12A and 12B are diagrams illustrating an embodiment of a puncture needle provided with a plurality of through-holes;

DETAILED DESCRIPTION

Figure 1:
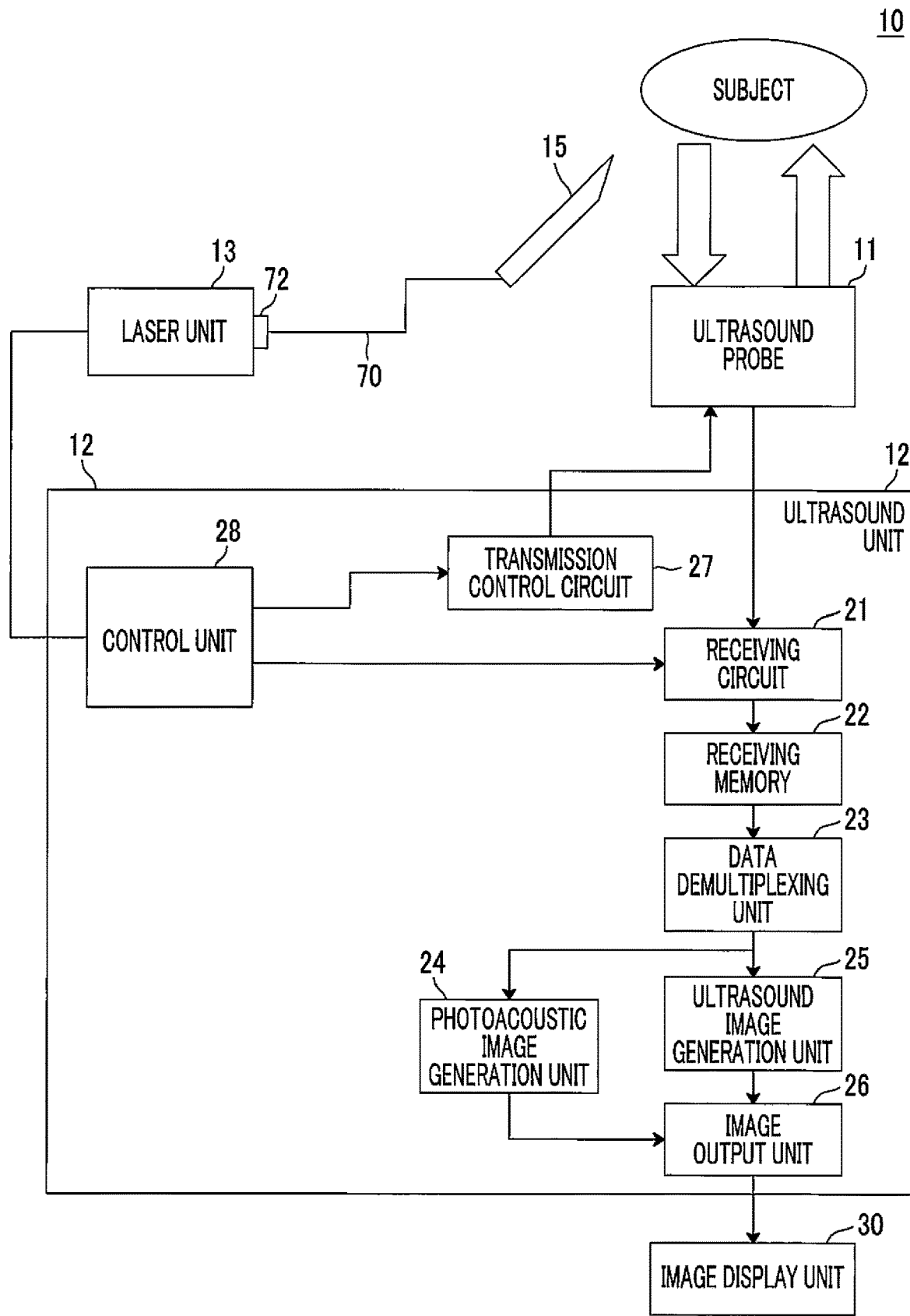
FIG. 1 is a block diagram schematically illustrating the configuration of a photoacoustic image generation apparatus comprising a puncture needle using a first embodiment of an insert according to the invention.

Hereinafter, a photoacoustic image generation apparatus 10 comprising a puncture needle using a first embodiment of an insert according to the invention will be described in detail with reference to the drawings. FIG. 1 is a diagram schematically illustrating the configuration of the photoacoustic image generation apparatus 10 according to this embodiment.

As illustrated in FIG. 1, the photoacoustic image generation apparatus 10 according to this embodiment comprises an ultrasound probe 11, an ultrasound unit 12, a laser unit 13, and a puncture needle 15. The puncture needle 15 and the laser unit 13 are connected by an optical cable 70 having an optical fiber. The optical cable 70 includes a portion extending from an optical fiber 14 in the puncture needle 15, which will be described below, and has an end at which a connector 72 is provided. The laser unit 13 is connected to the connector 72. The puncture needle 15 and the optical cable 70 are disposable. In addition, in this embodiment, ultrasonic waves are used as acoustic waves. However, the invention is not limited to the ultrasonic waves. Acoustic waves with an audible frequency may be used as long as an appropriate frequency can be selected according to, for example, an inspection target or measurement conditions. In addition, for example, a syringe or a transfusion tube is connected to the puncture needle 15 and can be used to inject a medical solution, which is not illustrated in FIG. 1.

The laser unit 13 corresponds to a light source unit according to the invention and comprises, for example, a semiconductor laser light source. Laser light emitted from a laser diode light source of the laser unit 13 is guided by the optical cable 70 and is incident on the puncture needle 15. The laser unit 13 according to this embodiment emits pulsed laser light in a near-infrared wavelength range. The near-infrared wavelength range means a wavelength range of about 700 nm to 2000 nm. In addition, in this embodiment, the laser diode light source is used. However, other laser light sources, such as a solid-state laser light source, a fiber laser light source, and a gas laser light source, may be used or, for example, a light emitting diode light source other than the laser light source may be used.

Figure 2:
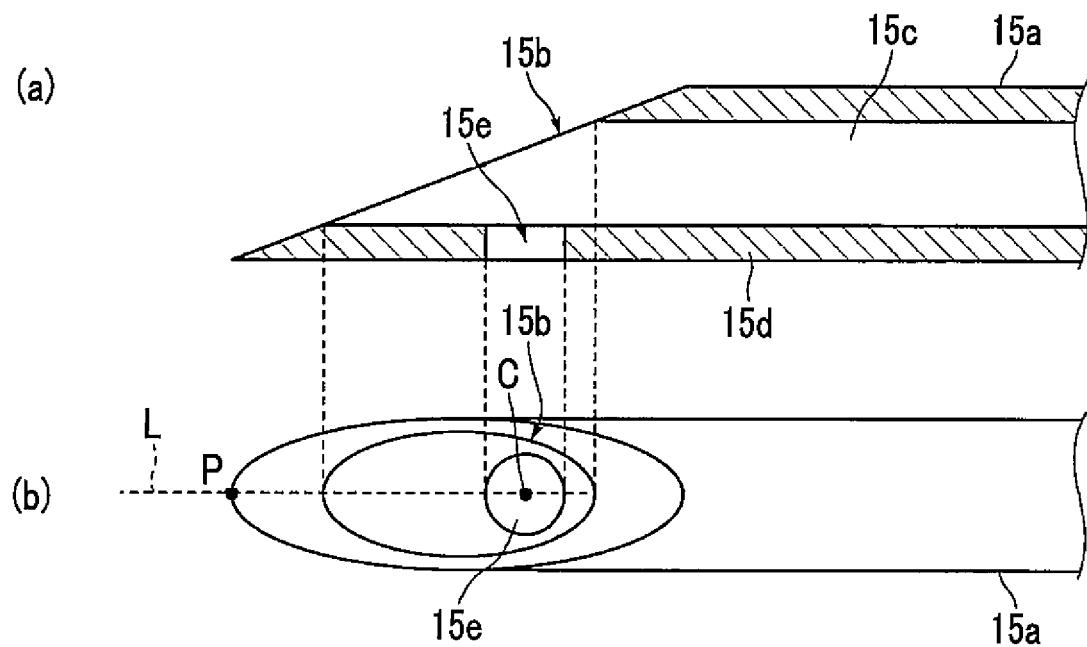
FIG. 2 is a diagram illustrating the configuration of a tip portion of a puncture needle main body in the puncture needle according to the first embodiment.

The puncture needle 15 is an embodiment of an insert according to the invention and is a needle of which at least a portion is inserted into a subject. FIG. 2 is a diagram illustrating the configuration of the vicinity of the tip of a puncture needle main body 15a (corresponding to an insert main body) which is a needle portion of the puncture needle 15. (a) of FIG. 2 is a cross-sectional view including a central axis that extends in a length direction of the puncture needle main body 15a and (b) of FIG. 2 is a top view in a case in which an opening 15b of the puncture needle main body 15a faces upward. As illustrated in (a) and (b) of FIG. 2, the puncture needle main body 15a is made of, for example, metal, has the opening 15b at the tip, and has a hollow shape. A through-hole 15e is formed in a wall portion 15d forming a hollow portion 15c of the puncture needle main body 15a. The diameter (inside diameter) of the hollow portion 15c of the puncture needle main body 15a may be so large that the optical fiber 14 which will be described below can be provided in the hollow portion 15c and is, for example, equal to or greater than 0.13 mm and equal to or less than 2.64 mm.

The through-hole 15e is a hole that passes from the hollow portion 15c of the puncture needle main body 15a to the outside of the puncture needle main body 15a and is preferably formed by high-precision laser machining. In this embodiment, the through-hole 15e is formed in a circular shape. The diameter of the through-hole 15e is preferably greater than the diameter of the optical fiber in terms of the propagation efficiency of photoacoustic waves, the fixation of a photoacoustic wave generation portion 16, and the strength of the puncture needle main body 15a which will be described below. The diameter of the through-hole 15e is desirably equal to or greater than 80 μm and is about 30% to 60% of the diameter of the hollow portion 15c of the puncture needle 15.

In addition, it is preferable that the center C of the through-hole 15e is in the vicinity of the tip of the puncture needle main body 15a. The vicinity of the tip of the puncture needle main body 15a means a position where the photoacoustic wave generation portion 16 which will be described below can generate photoacoustic waves capable of imaging the position of the tip of the puncture needle 15 with accuracy required for a needling operation in a case in which the photoacoustic wave generation portion 16 is disposed at the position of the through-hole 15e. It is preferable that the center C of the through-hole 15e is disposed in the opening 15b and is in the range of, for example, 0.2 mm to 2 mm from the tip of the puncture needle main body 15a.

In addition, it is desirable that the through-hole 15e is formed on a straight line L which extends in the length direction of the puncture needle main body 15a through a position P of the tip of the puncture needle main body 15a in the wall portion 15d forming the hollow portion 15c of the puncture needle main body 15a. Further, it is more preferable that the center C of the through-hole 15e is located on the straight line L.

Figure 3:
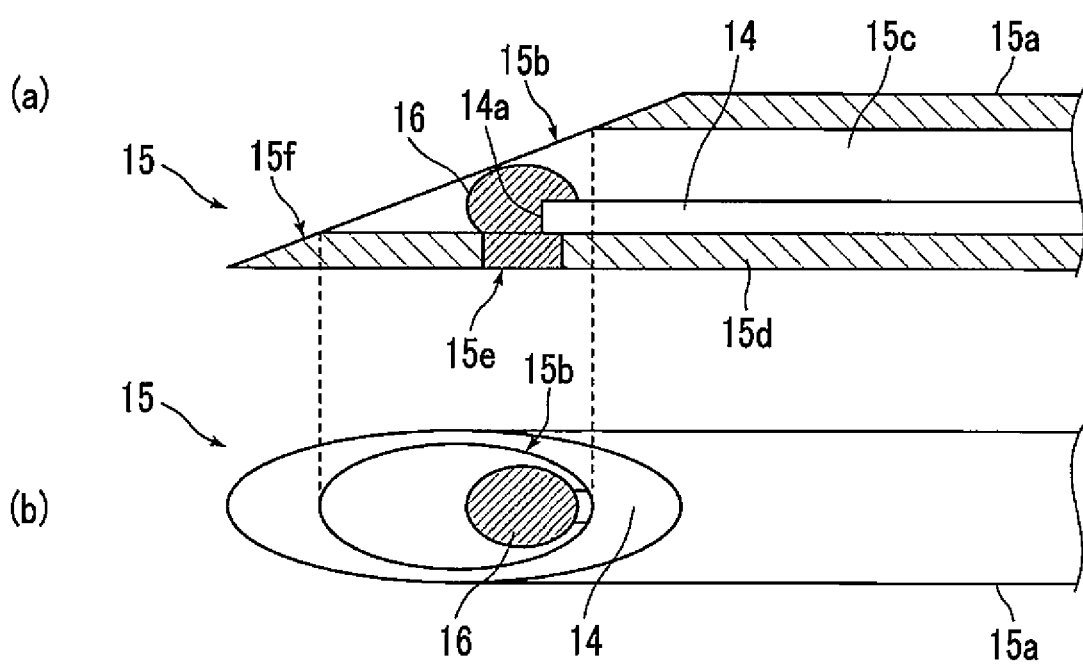
FIG. 3 is a diagram illustrating the configuration of the tip portion of the puncture needle according to the first embodiment.

FIG. 3 is a diagram illustrating the configuration of the puncture needle 15 in which the optical fiber 14 and the photoacoustic wave generation portion 16 are provided in the puncture needle main body 15a illustrated in FIG. 2. (a) of FIG. 3 is a cross-sectional view including a central axis that extends in the length direction of the puncture needle 15 and (b) of FIG. 3 is a top view in a case in which the opening 15b of the puncture needle 15 faces upward.

As illustrated in (a) and (b) of FIG. 3, the optical fiber 14 corresponding to a light guide member according to the invention is provided along the length direction of the puncture needle main body 15a in the hollow portion 15c of the puncture needle main body 15a. The photoacoustic wave generation portion 16 is provided at one end (light emission end) 14a of the optical fiber 14 which is close to the tip of the puncture needle main body 15a. Light guided by the optical fiber in the optical cable 70 is guided by the optical fiber 14. The optical fiber 14 may be coated. For example, polyimide, a fluorine resin, or an acrylic resin can be used for coating.

In the puncture needle 15 illustrated in FIG. 3, the through-hole 15e, the photoacoustic wave generation portion 16, and the tip of the optical fiber 14 are located in the puncture needle 15 such that the photoacoustic wave generation portion 16 does not protrude from a polished surface 15f of the puncture needle 15 as illustrated in (a) of FIG. 3. However, in practice, it is preferable that these components are disposed as close to the tip of the puncture needle 15 as possible in the range in which the photoacoustic wave generation portion 16 does not protrude from the polished surface 15f.

As described above, the photoacoustic wave generation portion 16 is provided at the light emission end 14a of the optical fiber 14, absorbs light emitted from the light emission end 14a, and generates photoacoustic waves. The photoacoustic wave generation portion 16 is fixed to the through-hole 15e. As a method for manufacturing the puncture needle 15 according to this embodiment, first, the optical fiber 14 is inserted into the hollow portion 15c of the puncture needle main body 15a such that the light emission end 14a of the optical fiber 14 is disposed on the through-hole 15e. Then, while a material forming the photoacoustic wave generation portion 16 is supplied to the light emission end 14a of the optical fiber 14, the through-hole 15e is filled with the material. After the filling, the material is cured.

The photoacoustic wave generation portion 16 is made of a material including a light absorber that absorbs light guided by the optical fiber 14 and a resin containing the light absorber. An example of the material forming the photoacoustic wave generation portion 16 is a synthetic resin, such as an epoxy resin, a fluorine resin, a silicone resin, or a polyurethane resin mixed with a black pigment. In addition, carbon black may be mixed with the synthetic resin. Further, for example, a thermosetting resin or a photocurable resin can be used as the synthetic resin. In FIG. 3, the photoacoustic wave generation portion 16 and the optical fiber 14 are drawn such that the photoacoustic wave generation portion 16 is larger than the optical fiber 14. However, the invention is not limited thereto. The size of the photoacoustic wave generation portion 16 may be substantially equal to the diameter of the optical fiber 14.

As described above, since the photoacoustic wave generation portion 16 is fixed to the through-hole 15e, the photoacoustic waves generated by the photoacoustic wave generation portion 16 can be emitted not only from the opening 15b but also from the through-hole 15e to the outside of the puncture needle 15. Therefore, it is possible to effectively propagate the photoacoustic waves on a surface side opposite to the opening 15b of the puncture needle 15. As a result, it is possible to detect the tip of the puncture needle 15 with high accuracy.

In addition, the photoacoustic waves generated by the photoacoustic wave generation portion 16 are emitted from the through-hole 15e without being reflected by the inner wall of the wall portion 15d forming the hollow portion 15c. Therefore, it is possible to suppress the generation of an artifact caused by the photoacoustic waves reflected by an inner metal surface (inner wall) of the puncture needle 15.

Furthermore, the through-hole 15e is filled with the material forming the photoacoustic wave generation portion 16 and the material is cured. Therefore, it is possible to obtain an anchor effect and to enhance the fixation of the photoacoustic wave generation portion 16.

Returning to FIG. 1, the ultrasound probe 11 corresponds to an acoustic wave detection unit according to the invention and includes, for example, a plurality of detector elements (ultrasound transducers) which are one-dimensionally arranged. The ultrasound probe 11 detects the photoacoustic waves generated from the photoacoustic wave generation portion 16 after the puncture needle 15 is inserted into the subject. The ultrasound probe 11 performs the transmission of acoustic waves (ultrasonic waves) to the subject and the reception of reflected acoustic waves (reflected ultrasonic waves) with respect to the transmitted ultrasonic waves, in addition to the detection of the photoacoustic waves. The transmission and reception of the ultrasonic waves may be performed at different positions. For example, ultrasonic waves may be transmitted from a position different from the position of the ultrasound probe 11 and the ultrasound probe 11 may receive the reflected ultrasonic waves with respect to the transmitted ultrasonic waves. The ultrasound probe 11 is not limited to a linear ultrasound probe and may be a convex ultrasound probe or a sector ultrasound probe.

The ultrasound unit 12 includes a receiving circuit 21, a receiving memory 22, a data demultiplexing unit 23, a photoacoustic image generation unit 24, an ultrasound image generation unit 25, an image output unit 26, a transmission control circuit 27, and a control unit 28. The ultrasound unit 12 typically includes a processor, a memory, and a bus. A program related to the generation of a photoacoustic image and the generation of an ultrasound image is incorporated into the memory of the ultrasound unit 12. The program is executed by the control unit 28 which is formed by a processor to implement the functions of the data demultiplexing unit 23, the photoacoustic image generation unit 24, the ultrasound image generation unit 25, and the image output unit 26. That is, each of these units is formed by the processor and the memory into which the program has been incorporated.

The hardware configuration of the ultrasound unit 12 is not particularly limited and can be implemented by an appropriate combination of, for example, a plurality of integrated circuits (ICs), a processor, an application specific integrated circuit (ASIC), a field-programmable gate array (FPGA), and a memory.

The receiving circuit 21 receives a detection signal output from the ultrasound probe 11 and stores the received detection signal in the receiving memory 22. The receiving circuit 21 typically includes a low-noise amplifier, a variable-gain amplifier, a low-pass filter, and an analog-to-digital converter (AD converter). The detection signal of the ultrasound probe 11 is amplified by the low noise amplifier. Then, gain adjustment corresponding to a depth is performed by the variable-gain amplifier and a high-frequency component of the detection signal is cut by the low-pass filter. Then, the detection signal is converted into a digital signal by the AD convertor and the digital signal is stored in the receiving memory 22. The receiving circuit 21 is formed by, for example, one integral circuit (IC).

The ultrasound probe 11 outputs a detection signal of the photoacoustic waves and a detection signal of the reflected ultrasonic waves. The AD-converted detection signals (sampling data) of the photoacoustic waves and the reflected ultrasonic waves are stored in the receiving memory 22. The data demultiplexing unit 23 reads the sampling data of the detection signal of the photoacoustic waves from the receiving memory 22 and transmits the sampling data to the photoacoustic image generation unit 24. In addition, the data demultiplexing unit 23 reads the sampling data of the reflected ultrasonic waves from the receiving memory 22 and transmits the sampling data to the ultrasound image generation unit 25.

The photoacoustic image generation unit 24 generates a photoacoustic image on the basis of the detection signal of the photoacoustic waves detected by the ultrasound probe 11. The generation of the photoacoustic image includes, for example, image reconfiguration, such as phasing addition, detection, and logarithmic conversion. The ultrasound image generation unit 25 generates an ultrasound image (reflected acoustic image) on the basis of the detection signal of the reflected ultrasonic waves detected by the ultrasound probe 11. The generation of the ultrasound image includes, for example, image reconfiguration, such as phasing addition, detection, and logarithmic conversion. The image output unit 26 outputs the photoacoustic image and the ultrasound image to an image display unit 30 such as a display device.

The control unit 28 controls each component in the ultrasound unit 12. For example, in a case in which a photoacoustic image is acquired, the control unit 28 transmits a trigger signal to the laser unit 13 such that the laser unit 13 emits laser light. In addition, the control unit 28 transmits a sampling trigger signal to the receiving circuit 21 to control, for example, the sampling start time of the photoacoustic waves with the emission of the laser light.

In a case in which an ultrasound image is acquired, the control unit 28 transmits an ultrasound transmission trigger signal for commanding the transmission of ultrasonic waves to the transmission control circuit 27. In a case in which the ultrasound transmission trigger signal is received, the transmission control circuit 27 directs the ultrasound probe 11 to transmit ultrasonic waves. The ultrasound probe 11 performs scanning while shifting acoustic lines one by one to detect the reflected ultrasonic waves. The control unit 28 transmits a sampling trigger signal to the receiving circuit 21 according to an ultrasound transmission time to start the sampling of the reflected ultrasonic waves.

Figure 4:
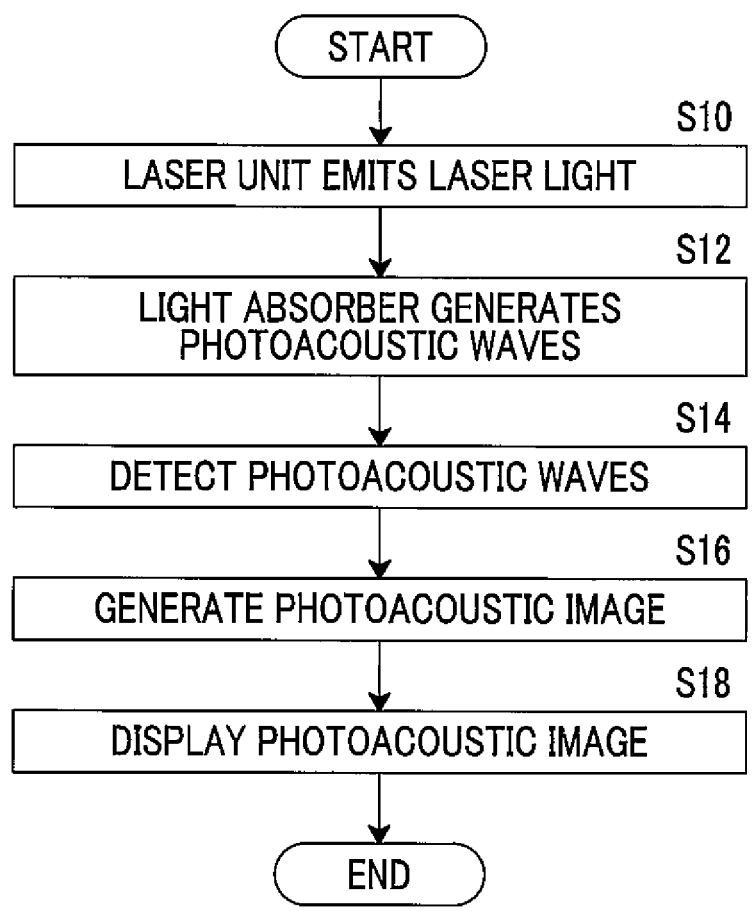
FIG. 4 is a flowchart illustrating a photoacoustic image generation process.

Next, the operation of the photoacoustic image generation apparatus 10 according to this embodiment will be described. First, a photoacoustic image generation process will be described with reference to a flowchart illustrated in FIG. 4.

In the photoacoustic image generation process, image acquisition conditions, such as a frame rate, the number of laser emission operations per frame, and the balance between the numbers of frames of reflected acoustic signals and photoacoustic image signals per frame, are stored in the memory (not illustrated) of the ultrasound unit 12 in advance. In addition, the control unit 28 determines light source driving conditions, such as a laser emission time, the number of laser pulses, and a current, so as to correspond to the image acquisition conditions and uses the light source driving conditions to drive the laser unit 13.

The photoacoustic image generation process starts in a state in which the connector 72 of the optical cable 70 connected to the puncture needle 15 is connected to the laser unit 13. The control unit 28 of the ultrasound unit 12 transmits a trigger signal to the laser unit 13. In a case in which the trigger signal is received, the laser unit 13 starts laser oscillation and emits pulsed laser light (S10). The pulsed laser light emitted from the laser unit 13 is guided by the optical cable 70 and is incident on the optical fiber 14 of the puncture needle 15. Then, the pulsed laser light is guided to the vicinity of the tip of the puncture needle 15 by the optical fiber 14 in the puncture needle 15 and is emitted to the photoacoustic wave generation portion 16. The photoacoustic wave generation portion 16 absorbs the pulsed laser light and generates photoacoustic waves (S12). In addition, in the photoacoustic image generation process, a user, such as a doctor, inserts the puncture needle 15 into the subject at any time such as before or after the driving of the laser unit 13.

The ultrasound probe 11 detects the photoacoustic waves generated from the photoacoustic wave generation portion 16 irradiated with the laser light (S14). A detection signal of the photoacoustic waves output from the ultrasound probe 11 is received by the receiving circuit 21 and the sampling data of the detection signal is stored in the receiving memory 22. The photoacoustic image generation unit 24 receives the sampling data of the detection signal of the photoacoustic waves through the data demultiplexing unit 23 and generates a photoacoustic image (S16). The photoacoustic image generation unit 24 may apply a color map to convert signal intensity in the photoacoustic image into a color. The photoacoustic image generated by the photoacoustic image generation unit 24 is input to the image output unit 26 and the image output unit 26 displays the photoacoustic image on the image display unit 30 (S18).

Figure 5:
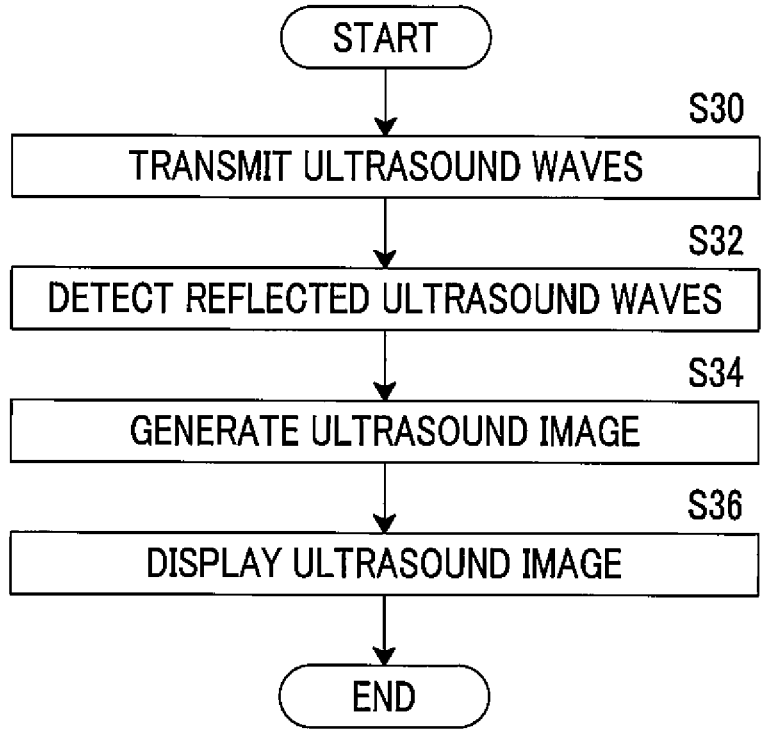
FIG. 5 is a flowchart illustrating an ultrasound image generation process.

Next, an ultrasound image generation process will be described with reference to a flowchart illustrated in FIG. 5. First, the control unit 28 transmits an ultrasound transmission trigger signal to the transmission control circuit 27 and the transmission control circuit 27 directs the ultrasound probe 11 to transmit ultrasonic waves in response to the ultrasound transmission trigger signal (S30). The ultrasound probe 11 transmits ultrasonic waves and then detects reflected ultrasonic waves (S32). Then, a detection signal of the reflected ultrasonic waves is received by the receiving circuit 21 and the sampling data of the detection signal is stored in the receiving memory 22. The ultrasound image generation unit 25 receives the sampling data of the detection signal of the ultrasonic waves through the data demultiplexing unit 23 and generates an ultrasound image (S34). The ultrasound image generation unit 25 may apply a color map to convert signal intensity in the ultrasound image into a color. The ultrasound image generated by the ultrasound image generation unit 25 is input to the image output unit 26 and the image output unit 26 displays the ultrasound image on the image display unit 30 (S36).

The image display unit 30 may display a composite image of the photoacoustic image and the ultrasound image. In this case, it is possible to check the position of the tip of the puncture needle 15 in a living body and thus to accurately perform a safe needling operation. In addition, in this embodiment, as described above, photoacoustic waves can also be emitted from the through-hole 15e provided in the puncture needle 15. Therefore, it is possible to improve the visibility of the tip of the puncture needle 15.

Next, a puncture needle 15 using another embodiment of the insert according to the invention will be described.

In the puncture needle 15 according to the first embodiment, the through-hole 15e formed in the puncture needle main body 15a is formed in a circular shape. However, in the puncture needle 15 according to a second embodiment, a through-hole 15e is formed in an elliptical shape.

Figure 6:
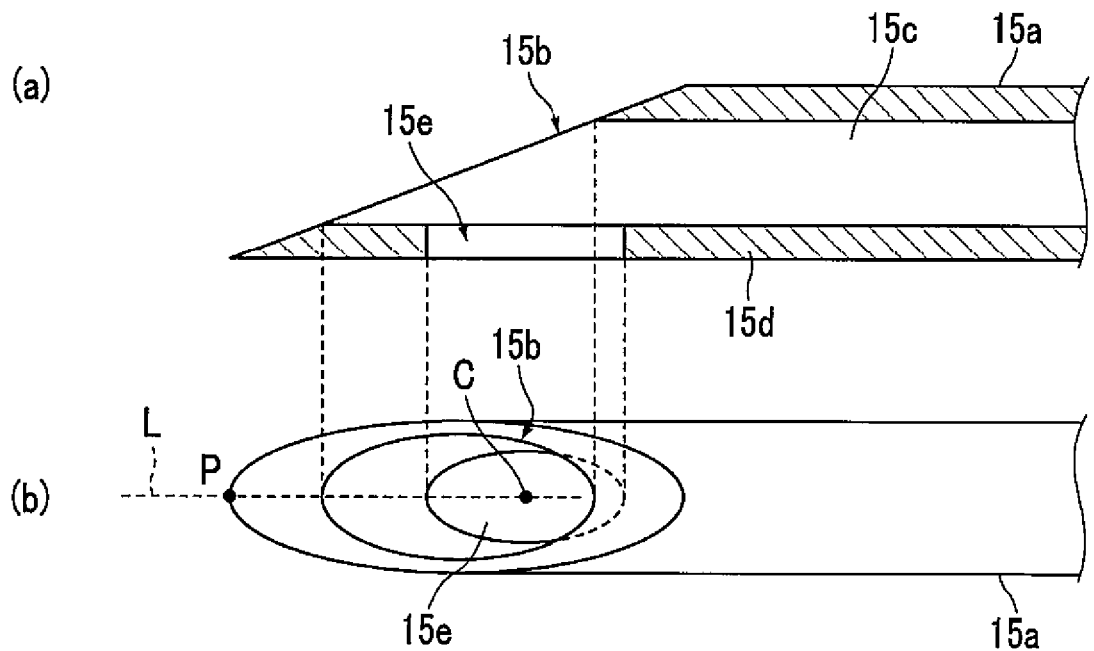
FIG. 6 is a diagram illustrating the configuration of a tip portion of a puncture needle main body in a puncture needle according to a second embodiment.

(a) of FIG. 6 is a cross-sectional view illustrating a puncture needle main body 15a of the puncture needle 15 according to the second embodiment (a cross-sectional view including a central axis that extends in a length direction of the puncture needle main body 15a) and (b) of FIG. 6 is a top view in a case in which an opening 15b of the puncture needle main body 15a faces upward.

As illustrated in (a) and (b) of FIG. 6, the through-hole 15e of the puncture needle 15 according to the second embodiment is formed in an elliptical shape which extends in the length direction rather than in a direction perpendicular to the length direction of the puncture needle main body 15a. It is desirable that the longest diameter of the through-hole 15e is 0.3 mm to 2 mm greater than the shortest diameter in terms of the propagation efficiency of photoacoustic waves, the fixation of a photoacoustic wave generation portion 16, and the strength of the puncture needle main body 15a.

Similarly to the case in which the through-hole 15e has a circular shape, it is preferable that the center C of the through-hole 15e is in the vicinity of the tip of the puncture needle main body 15a. For example, it is preferable that the center C of the through-hole 15e is in the range of 0.2 mm to 2 mm from the tip of the puncture needle main body 15a.

In addition, it is desirable that the through-hole 15e is formed on a straight line L which extends in the length direction of the puncture needle main body 15a through a position P of the tip of the puncture needle main body 15a in a wall portion 15d forming the hollow portion 15c of the puncture needle main body 15a. Further, it is more preferable that the center C of the through-hole 15e is located on the straight line L.

Figure 7:
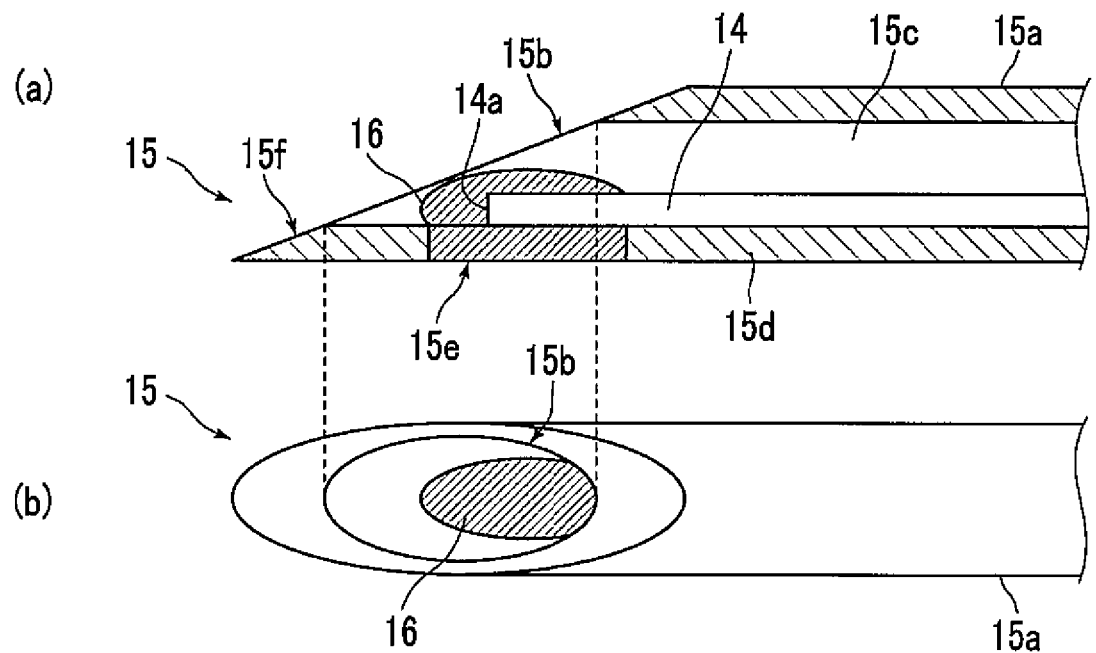
FIG. 7 is a diagram illustrating the configuration of the tip portion of the puncture needle according to the second embodiment.

FIG. 7 is a diagram illustrating the configuration of the puncture needle 15 in which the optical fiber 14 and the photoacoustic wave generation portion 16 are provided in the puncture needle main body 15a illustrated in FIG. 6. (a) of FIG. 7 is a cross-sectional view including the central axis that extends in the length direction of the puncture needle 15 and (b) of FIG. 7 is a top view in a case in which the opening 15b of the puncture needle 15 faces upward. The configuration is the same as that in the case in which the through-hole 15e has a circular shape except that the shape of the through-hole 15e changes from the circular shape to the elliptical shape. As illustrated in FIGS. 6 and 7, since the through-hole 15e has the elliptical shape, it is possible to increase the opening area of the through-hole 15e. Therefore, it is possible to effectively propagate the photoacoustic waves on a surface side opposite to the opening 15b of the puncture needle 15. In addition, an anchor effect can be improved more than that in a case in which the through-hole 15e has the circular shape.

In the puncture needle 15 illustrated in FIG. 7, the through-hole 15e, the photoacoustic wave generation portion 16, and the tip of the optical fiber 14 are located in the puncture needle 15 such that the photoacoustic wave generation portion 16 does not protrude from a polished surface 15f of the puncture needle 15 as illustrated in (a) of FIG. 7. However, in practice, it is preferable that these components are disposed as close to the tip of the puncture needle 15 as possible in the range in which the photoacoustic wave generation portion 16 does not protrude from the polished surface 15f.

Next, a puncture needle 15 according to a third embodiment will be described. In the puncture needle 15 according to the first embodiment, the through-hole 15e is filled with the material forming the photoacoustic wave generation portion 16 while the material is supplied to the light emission end of the optical fiber 14 to form the photoacoustic wave generation portion 16 such that the photoacoustic wave generation portion 16 and the tip portion of the optical fiber 14 are fixed to the wall portion 15d of the puncture needle main body 15a. However, in the puncture needle 15 according to the third embodiment, the optical fiber 14 provided with the photoacoustic wave generation portion 16 is fixed to the wall portion 15d of the puncture needle main body 15a by a synthetic resin which is an adhesive.

Figure 8:
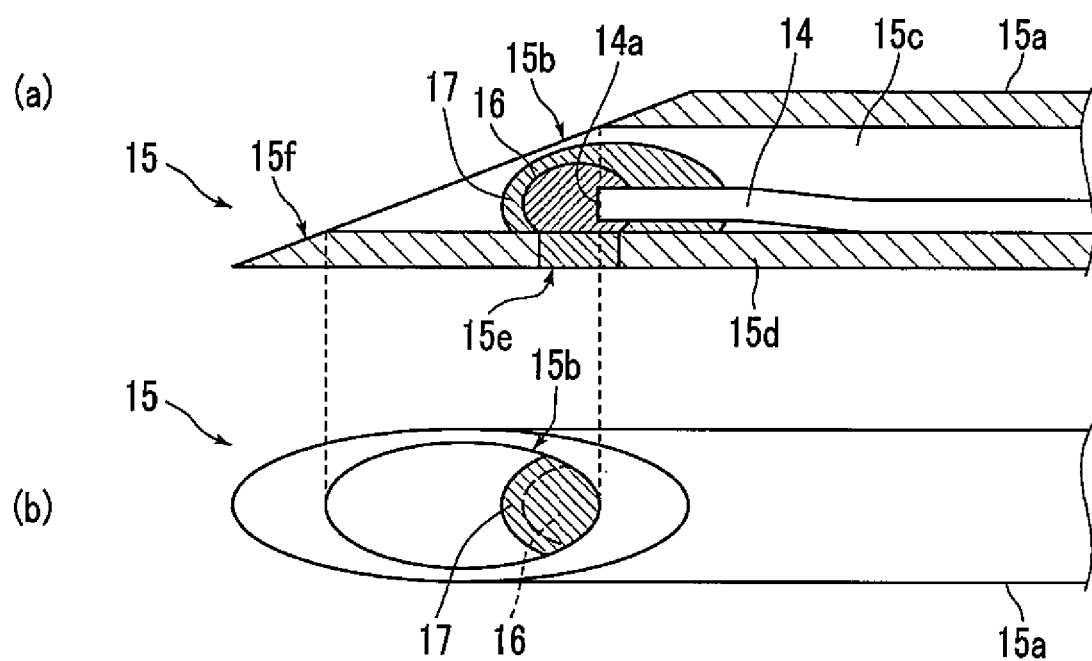
FIG. 8 is a diagram illustrating the configuration of a tip portion of a puncture needle according to a third embodiment.

FIG. 8 is a diagram illustrating an example of the puncture needle 15 according to third embodiment. (a) of FIG. 8 is a cross-sectional view illustrating a central axis which extends in the length direction of the puncture needle 15 and (b) of FIG. 8 is a top view in a case in which the opening 15b of the puncture needle 15 faces upward. As a method for manufacturing the puncture needle 15 according to the third embodiment, first, the photoacoustic wave generation portion 16 is formed at the light emission end 14a of the optical fiber 14. Then, the optical fiber 14 provided with the photoacoustic wave generation portion 16 is inserted into the hollow portion 15c of the puncture needle main body 15a such that the photoacoustic wave generation portion 16 is disposed on the through-hole 15e. Then, while an adhesive resin 17 is supplied to the photoacoustic wave generation portion 16, the through-hole 15e is filled with the adhesive resin 17. After the filling, the adhesive resin 17 is cured. A thermosetting resin and a photocurable resin can be used as the adhesive resin 17. However, it is preferable to use the photocurable resin that is more simply processed. For example, a resin that is cured by irradiation with visible light or a resin that is cured by irradiation with ultraviolet light can be used as the photocurable resin.

In the puncture needle 15 illustrated in FIG. 8, the through-hole 15e, the photoacoustic wave generation portion 16, the adhesive resin 17, and the tip of the optical fiber 14 are located in the puncture needle 15 such that the adhesive resin 17 does not protrude from the polished surface 15f of the puncture needle 15 as illustrated in (a) of FIG. 8. However, in practice, it is preferable that these components are disposed as close to the tip of the puncture needle 15 as possible in the range in which the adhesive resin 17 does not protrude from the polished surface 15f. In particular, since the photocurable resin is irradiated with light in a fixed range, it is preferable that the photocurable resin is not too far inside the puncture needle main body 15a.

As such, the optical fiber 14 provided with the photoacoustic wave generation portion 16 is inserted into the hollow portion 15c of the puncture needle main body 15a and the photoacoustic wave generation portion 16 is disposed so as to be fitted to the through-hole 15e. Therefore, it is easy to control the disposition of the photoacoustic wave generation portion 16 and to dispose the light emission end 14a of the optical fiber 14 in the photoacoustic wave generation portion 16 in the vicinity of the center of the through-hole 15e. As a result, it is possible to effectively propagate the photoacoustic waves on a surface side opposite to the opening 15b of the puncture needle 15.

Further, in a case in which the optical fiber 14 is inserted into the hollow portion 15c of the puncture needle main body 15*a*, the light emission end 14*a* of the optical fiber 14 is protected by the photoacoustic wave generation portion 16. Therefore, the light emission end 14*a* of the optical fiber 14 can be prevented from being broken by collision with an insertion hole for the optical fiber 14 in the puncture needle main body 15*a* or the inner wall of the puncture needle main body 15*a*.

Figure 9:
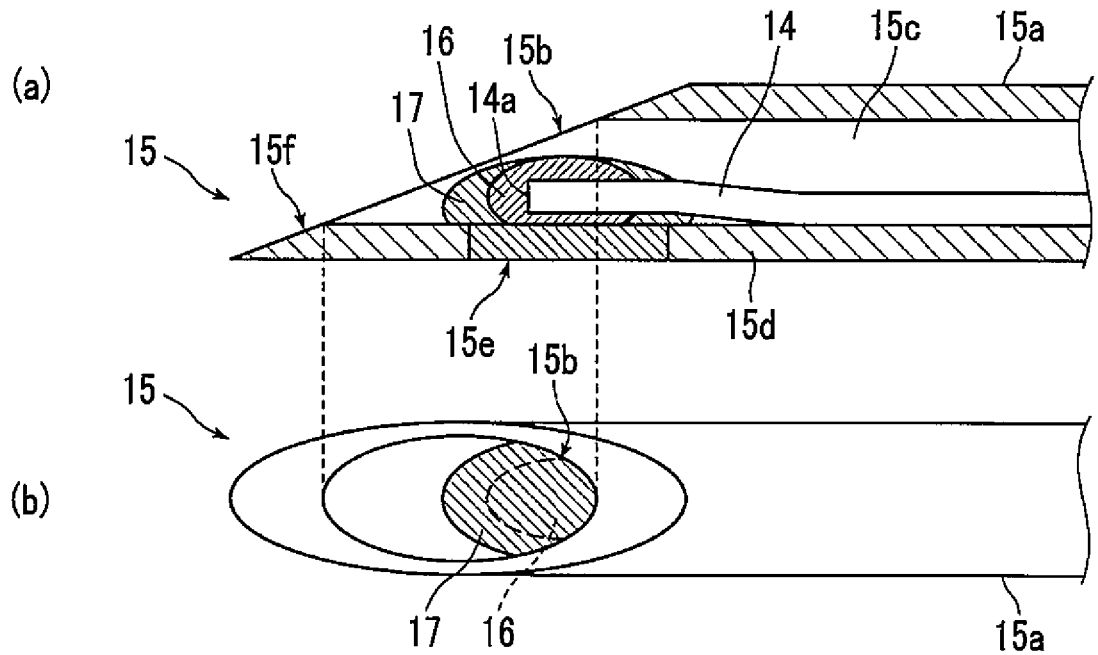
FIG. 9 is a diagram illustrating the configuration of a tip portion of a puncture needle according to a fourth embodiment.

In the puncture needle 15 according to the third embodiment, the through-hole 15*e* may be formed in an elliptical shape. FIG. 9 is a diagram illustrating a puncture needle 15 according to a fourth embodiment in which the through-hole 15*e* of the puncture needle 15 according to the third embodiment is formed in an elliptical shape. (a) of FIG. 9 is a cross-sectional view including a central axis which extends in the length direction of the puncture needle 15 according to the fourth embodiment and (b) of FIG. 9 is a top view in a case in which the opening 15*b* of the puncture needle 15 faces upward. The puncture needle 15 according to the fourth embodiment and a method for manufacturing the puncture needle 15 are the same as those in the third embodiment except that the through-hole 15*e* is formed in an elliptical shape. For example, the size and disposition of the through-hole 15*e* in a case in which the through-hole 15*e* is formed in an elliptical shape are the same as those in the puncture needle 15 according to the second embodiment illustrated in FIG. 7.

In the puncture needle 15 illustrated in FIG. 9, the through-hole 15*e*, the photoacoustic wave generation portion 16, the adhesive resin 17, and the tip of the optical fiber 14 are located in the puncture needle 15 such that the adhesive resin 17 does not protrude from the polished surface 15*f* of the puncture needle 15 as illustrated in (a) of FIG. 9. However, in practice, it is preferable that these components are disposed as close to the tip of the puncture needle 15 as possible in the range in which the adhesive resin 17 does not protrude from the polished surface 15*f*. In particular, since a photocurable resin is irradiated with light in a fixed range, it is preferable that the photocurable resin is not too far inside the puncture needle main body 15*a*.

Next, a puncture needle 15 according to a fifth embodiment will be described. In the puncture needle 15 according to the first embodiment illustrated in FIG. 3, a black resin is used as the material forming the photoacoustic wave generation portion 16. However, in the puncture needle 15 according to the fifth embodiment, a material that absorbs laser light emitted from the laser unit 13 and transmits visible light is used as the material forming the photoacoustic wave generation portion 16.

Figure 10:
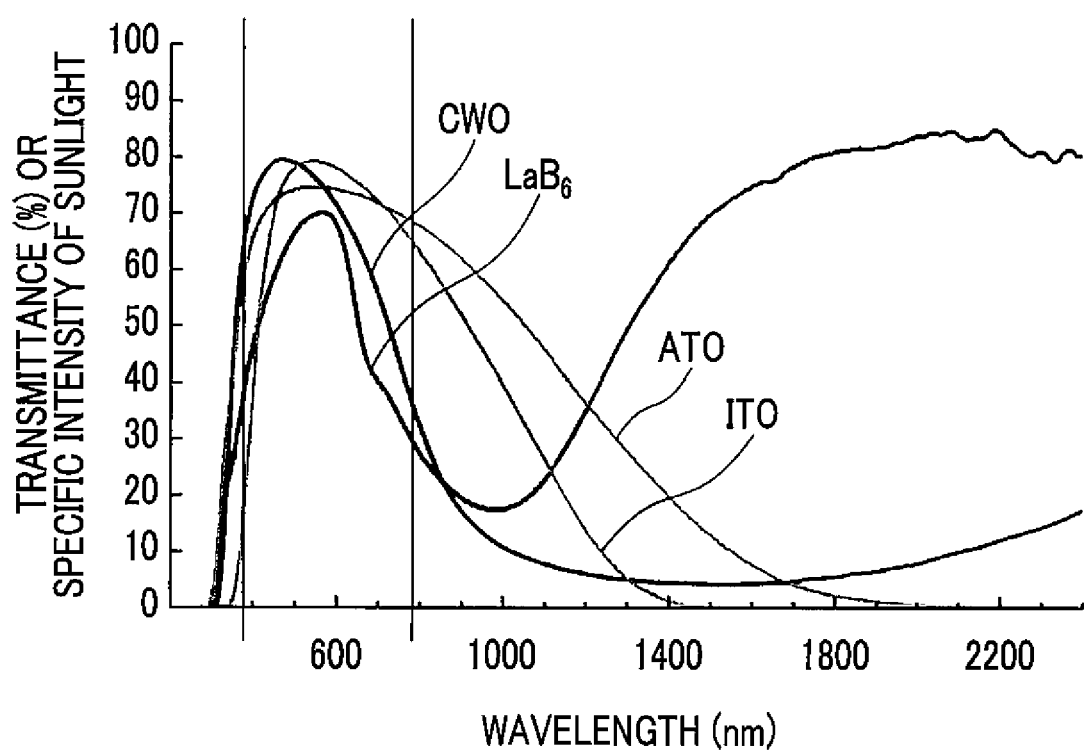
FIG. 10 is a diagram illustrating the light transmission characteristics of CWO, $LaB_6$, ATO, and ITO.

For example, in a case in which near-infrared light is used as laser light, a material obtained by mixing a pigment that absorbs near-infrared light and transmits visible light with a synthetic resin can be used as the material. For example, cesium tungsten oxide (CWO), lanthanum hexaboride (LaB$_6$), antimony tin oxide (ATO), and indium tin oxide (ITO) can be used as the pigment that absorbs near-infrared light and transmits visible light. FIG. 10 is a diagram illustrating the light transmission characteristics of CWO, LaB$_6$, ATO, and ITO. In addition, titanium black, such as titanium oxide (TiO), may be used. FIG. 11 is a diagram illustrating the light transmission characteristics of TiO. FIG. 11 also illustrates the light transmission characteristics of carbon black for comparison. In addition, the transmittance of visible light through the photoacoustic wave generation portion 16 may be 40% or more with respect to at least a portion of the wavelength range of visible light. The configuration including a method for manufacturing the puncture needle 15 is the same as that in the puncture needle 15 according to the first embodiment illustrated in FIG. 3 except the material forming the photoacoustic wave generation portion 16. In addition, the transmittance of light can be controlled by changing the mixture concentration of the pigment with the resin. The material can be applied onto a slide glass with the same thickness as that applied to the optical fiber 14 and the transmittance can be measured, for example, a spectrophotometer and can be determined.

As such, since a material that absorbs laser light emitted from the laser unit 13 and transmits visible light is used as the material forming the photoacoustic wave generation portion 16, the material can be used to detect the cutting of the optical fiber 14, which will be described below. That is, for example, in a case in which the optical fiber 14 is not cut, light guided by the optical fiber 14 is emitted from the light emission end 14*a* of the optical fiber 14 and is transmitted through the photoacoustic wave generation portion 16. The light can be observed through the opening 15*b* of the puncture needle 15. In contrast, for example, in a case in which the optical fiber 14 is cut, the light guided by the optical fiber 14 leaks from the cut portion. As a result, light is not capable of being observed through the opening 15*b* of the puncture needle 15 or only light with low intensity is capable of being observed. As such, the visible light emitted from the opening 15*b* of the puncture needle 15 is observed to detect the cutting of the optical fiber 14. In addition, a configuration for detecting the cutting of the optical fiber 14 will be described in detail below.

In the puncture needle 15 according to the fifth embodiment, the through-hole 15*e* may be formed in an elliptical shape as in the puncture needle 15 according to the second embodiment. A puncture needle 15 according to a sixth embodiment in which a through-hole 15*e* is formed in an elliptical shape and a method for manufacturing the puncture needle 15 are the same as those in the second embodiment illustrated in FIG. 7 except a material forming the photoacoustic wave generation portion 16. In addition, for example, the size and disposition of the through-hole 15*e* in a case in which the through-hole 15*e* is formed in an elliptical shape are the same as those in the puncture needle 15 according to the second embodiment illustrated in FIG. 7.

Next, a puncture needle 15 according to a seventh embodiment will be described. In the puncture needle 15 according to the seventh embodiment, a material that absorbs laser light emitted from the laser unit 13 and transmits visible light is used as a material forming the photoacoustic wave generation portion 16 as in the puncture needle 15 according to the fifth embodiment and the optical fiber 14 provided with the photoacoustic wave generation portion 16 made of the material is fixed to the wall portion 15*d* of the puncture needle main body 15*a* by a synthetic resin which is an adhesive as in the puncture needle 15 according to the third embodiment illustrated in FIG. 8. In this case, the puncture needle 15 and a method for manufacturing the puncture needle 15 according to this embodiment are the same as those in the third embodiment illustrated in FIG. 8 except that the material forming the photoacoustic wave generation portion 16 is different. However, in a case in which a visible light curable resin is used as the adhesive resin 17, it is possible to irradiate the adhesive resin 17 through the photoacoustic wave generation portion 16 with visible light guided by the optical fiber 14 since the photoacoustic wave generation portion 16 is made of the material that transmits visible light and thus to cure the adhesive resin 17. In addition, in a case in which the above-mentioned CWO, LaB$_6$, ATO, and TiO are used as the pigment included in the photoacoustic wave generation portion 16, an ultraviolet curable resin can also be used as the adhesive resin 17 since the photoacoustic wave generation portion 16 transmits ultraviolet light.

In the puncture needle 15 according to the seventh embodiment, the through-hole 15e may be formed in an elliptical shape as in the puncture needle 15 according to the second embodiment. A puncture needle 15 according to an eighth embodiment in which a through-hole 15e is formed in an elliptical shape and a method for manufacturing the puncture needle 15 are the same as those in the seventh embodiment except that the through-hole 15e is formed in an elliptical shape. In addition, for example, the size and disposition of the through-hole 15e are the same as those in the puncture needle 15 according to the second embodiment illustrated in FIG. 7.

Next, a puncture needle 15 according to a ninth embodiment will be described. In the puncture needle 15 according to the ninth embodiment, a photocurable resin including a pigment that absorbs laser light emitted from the laser unit 13 and transmits visible light is used as the material forming the photoacoustic wave generation portion 16 in the puncture needle 15 according to the first embodiment illustrated in FIG. 3. As described above, for example, CWO, LaB$_6$, ATO, ITO, and TiO can be used as the pigment that absorbs laser light (near-infrared light) and transmits visible light. In addition, a visible light curable resin and an ultraviolet curable resin can be used as the photocurable resin. In a case in which the visible light curable resin is used, the visible light curable resin is irradiated with visible light guided by the optical fiber 14 to form the photoacoustic wave generation portion 16. In addition, in a case in which CWO, LaB$_6$, ATO, and TiO are used as the pigment, an ultraviolet curable resin can also be used as the photocurable resin since it also transmits ultraviolet light. The puncture needle 15 according to the ninth embodiment is the same as the puncture needle 15 according to the first embodiment except the material forming the photoacoustic wave generation portion 16.

As a method for manufacturing the puncture needle 15 according to the ninth embodiment, first, the optical fiber 14 is inserted into the hollow portion 15c of the puncture needle main body 15a such that the light emission end 14a of the optical fiber 14 is disposed on the through-hole 15e. Then, while a material including the pigment and the photocurable resin is supplied to the light emission end 14a of the optical fiber 14, the through-hole 15e is filled with the material. The photocurable resin is irradiated with light guided by the optical fiber 14 and is cured.

In the puncture needle 15 according to the ninth embodiment, the through-hole 15e may be formed in an elliptical shape as in the puncture needle 15 according to the second embodiment. A puncture needle 15 according to a tenth embodiment in which a through-hole 15e is formed in an elliptical shape and a method for manufacturing the puncture needle 15 are the same as those in the ninth embodiment except that the through-hole 15e is formed in an elliptical shape. In addition, for example, the size and disposition of the through-hole 15e are the same as those in the puncture needle 15 according to the second embodiment illustrated in FIG. 7.

As in the puncture needles 15 according to the ninth and tenth embodiments, the photocurable resin is irradiated with light guided by the optical fiber 14 and is cured to form and fix the photoacoustic wave generation portion 16, which makes it possible to omit, for example, a heating process for curing a synthetic resin again.

In the puncture needles 15 according to the first to tenth embodiments, the through-hole 15e may be formed in a tapered shape. That is, in the through-hole 15e, the size of an opening close to the inner wall of the puncture needle main body 15a may be larger than the size of an opening close to the outer wall.

In the puncture needles 15 according to the fifth to tenth embodiments, the cutting of the optical fiber can be detected even in a case in which the through-hole 15e is not provided in the puncture needle 15.

In the puncture needles 15 according to the first to tenth embodiments, one through-hole 15e is provided in the puncture needle main body 15a. However, the invention is not limited thereto. A plurality of through-holes may be provided. FIGS. 12A and 12B illustrate an embodiment of a puncture needle in which two through-holes are provided in a puncture needle main body. FIG. 12A is a cross-sectional view including a central axis that extends in the length direction of a puncture needle 18 having two through-holes 18e and FIG. 12B is a diagram illustrating the puncture needle 18 illustrated in FIG. 12A as viewed from the direction of an arrow Y.

In the puncture needle 18 illustrated in FIGS. 12A and 12B, the through-holes 18e are provided at the positions that face each other in the puncture needle main body 18a. Then, the photoacoustic wave generation portion 16 and the light emission end 14a of the optical fiber 14 are disposed with respect to one of the two through-holes 18e. The photoacoustic wave generation portion 16 is the same as that in the puncture needle 15 according to the first embodiment.

As a method for manufacturing the puncture needle 18 illustrated in FIGS. 12A and 12B, the optical fiber 14 is inserted into the puncture needle main body 18a. While the position of the light emission end 14a of the optical fiber 14 is checked through the through-hole 18e (hereinafter, referred to as a second through-hole 18e) opposite to the through-hole 18e (hereinafter, referred to as a first through-hole 18e) with respect to which the photoacoustic wave generation portion 16 is provided, the light emission end 14a of the optical fiber 14 is disposed on the first through-hole 18e. Then, while the material forming the photoacoustic wave generation portion 16 is supplied to the light emission end 14a of the optical fiber 14 through the second through-hole 18e, the first through-hole 18e is filled with the material. After the filling, the material is cured.

In the configuration in which two through-holes 18e are provided as in the puncture needle 18 illustrated in FIGS. 12A and 12B, it is possible to propagate photoacoustic waves from the two through-holes 18e. Therefore, it is possible to detect the tip of the puncture needle 18 with high sensitivity.

In the puncture needle 18 illustrated in FIGS. 12A and 12B, two through-holes 18e are provided. However, the number of through-holes 18e is not limited to 2. Four through-holes may be provided in directions perpendicular to each other.

In the puncture needles 15 according to the second to tenth embodiments, similarly to the above, a plurality of through-holes may be formed in the puncture needle main body 15a.

Figure 13:
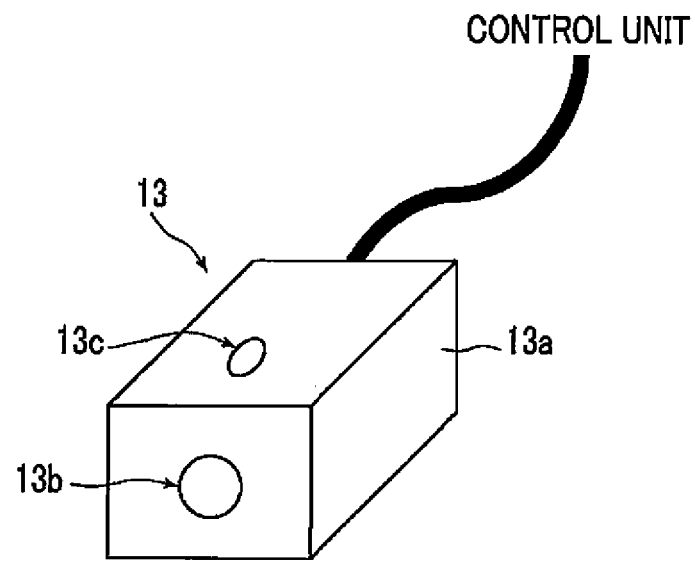
FIG. 13 is a diagram illustrating the outward appearance of an example of a laser unit used to detect cutting.

Next, a configuration for detecting the cutting of the optical fiber 14 in a case in which the puncture needles 15 according to the fifth to tenth embodiments are used will be described. FIG. 13 is a diagram illustrating the outward appearance of an example of the laser unit 13 used to detect the cutting and FIG. 14 is a diagram illustrating the internal configuration of an example of the laser unit 13 used to detect the cutting.

The laser unit 13 for detecting the cutting illustrated in FIG. 13 comprises a housing 13a having a rectangular parallelepiped shape and a light source-side connector 13b to which the connector 72 of the optical cable 70 is connected is provided in a side surface of the housing 13a. In addition, the details of a connection mechanism are not illustrated. Further, a light emission portion 13c from which visible light for detecting cutting is emitted is provided in an upper surface of the housing 13a.

Figure 14:
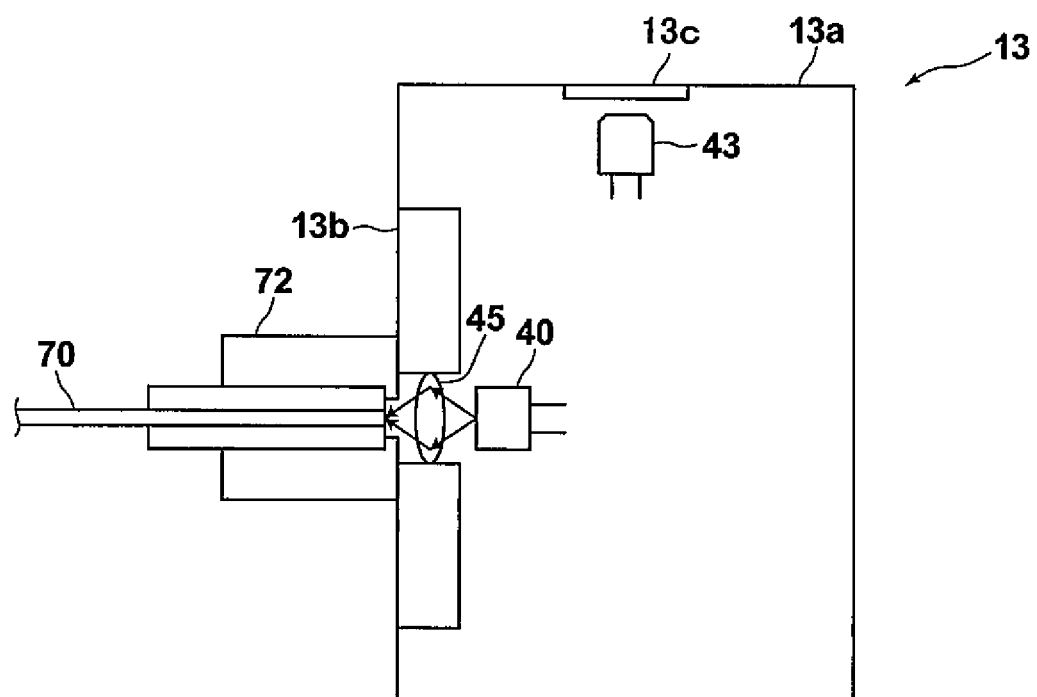
FIG. 14 is a diagram illustrating the internal configuration of the example of the laser unit used to detect cutting.

As illustrated in FIG. 14, a pulsed laser light source 40 that emits pulsed laser light with which the photoacoustic wave generation portion 16 of the puncture needle 15 is irradiated, a condensing lens 45 that makes the pulsed laser light emitted from the pulsed laser light source 40 incident on the optical fiber in the optical cable 70, and a visible light source 43 that emits visible light for detecting cutting are provided in the housing 13a.

The light emission portion 13c is made of a member that is transparent with respect to the visible light emitted from the visible light source 43 and transmits the visible light emitted from the visible light source 43 such that the visible light is emitted from the surface of the housing 13a to the outside.

In a case in which the cutting of the optical fiber 14 in the puncture needle 15 is detected, a user, such as a doctor, brings a light incident end of the optical fiber 14 in the puncture needle 15 close to the light emission portion 13c and visible light emitted from the light emission portion 13c is incident from the light incident end of the optical fiber 14.

At that time, as described above, in a case in which the optical fiber 14 is not cut, light guided by the optical fiber 14 is emitted from the light emission end 14a of the optical fiber 14 and is transmitted through the photoacoustic wave generation portion 16. The light can be observed through the opening 15b of the puncture needle 15. In contrast, for example, in a case in which the optical fiber 14 is cut, the light guided by the optical fiber 14 leaks from the cut portion. As a result, light is not capable of being observed through the opening 15b of the puncture needle 15 or only light with low intensity is capable of being observed. As such, the visible light emitted from the opening 15b of the puncture needle 15 is observed to detect the cutting of the optical fiber 14.

The emission of visible light from the visible light source 43 is controlled by the control unit 28 of the laser unit 13 connected to the ultrasound unit 12. Specifically, for example, the control unit 28 may direct the visible light source 43 to emit visible light in response to a cutting detection command input by the user through a predetermined input device (not illustrated). Alternatively, in a case in which the user inputs a command to emit pulsed laser light from the pulsed laser light source 40 in a state in which the visible light source 43 does not emit visible light, the control unit 28 may stop the emission of visible light from the visible light source 43. Alternatively, the connection of the connector 72 to the light source-side connector 13b may be automatically detected and the emission of visible light may be stopped.

In addition, the configuration of the laser unit 13 for detecting cutting is not limited to the configurations illustrated in FIGS. 13 and 14. FIGS. 15 to 18 are diagrams illustrating the internal configurations of other embodiments of the laser unit 13 for detecting cutting. Basically, FIGS. 15 to 18 illustrate the configurations that make visible light emitted from the visible light source 43 incident on the optical fiber in the optical cable 70 connected to the light source-side connector 13b.

Figure 15:
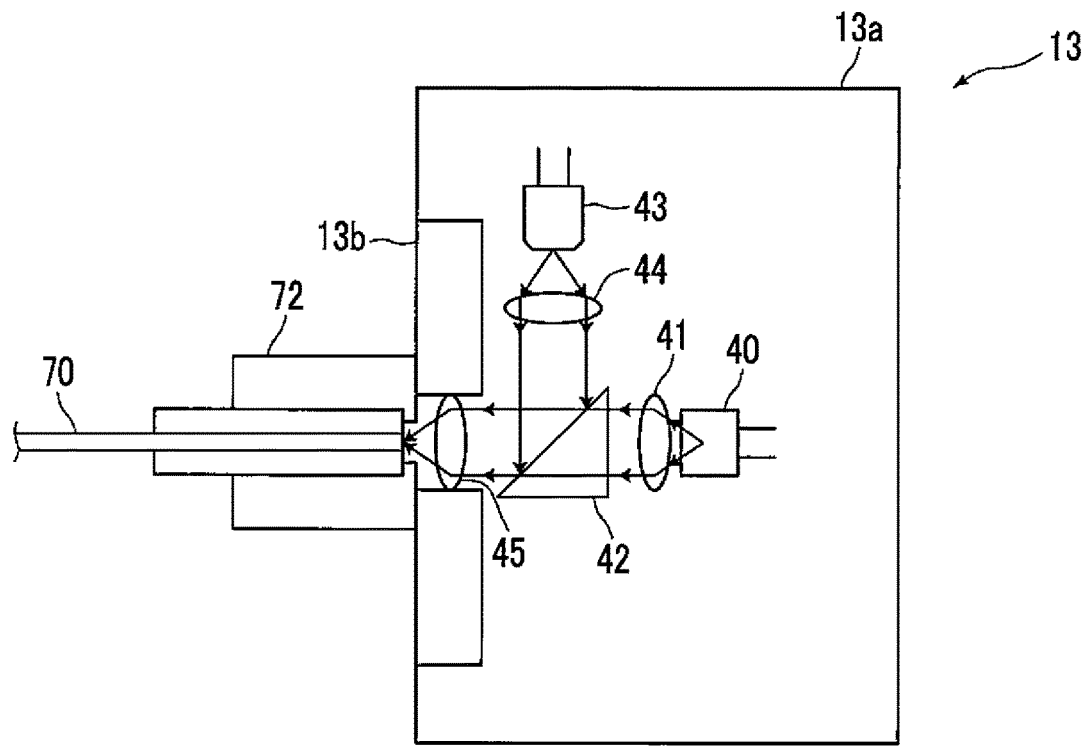
FIG. 15 is a diagram illustrating the internal configuration of another example of the laser unit used to detect cutting.

The laser unit 13 for detecting cutting illustrated in FIG. 15 further comprises a collimating lens 41 that collimates pulsed laser light emitted from the pulsed laser light source 40, a multiplexing prism 42 that transmits the pulsed laser light emitted from the pulsed laser light source 40 so as to be incident on the condensing lens 45 and reflects visible light emitted from the visible light source 43 so as to be incident on the condensing lens 45, and a collimating lens 44 that makes the visible light emitted from the visible light source 43 incident on the multiplexing prism 42. In the laser unit 13 illustrated in FIG. 15, the collimating lenses 41 and 44, the multiplexing prism 42, and the condensing lens 45 correspond to optical members according to the invention.

The visible light incident on the optical cable 70 is guided by the optical fiber in the optical cable 70 and is then guided by the optical fiber 14 in the puncture needle 15. Then, the visible light emitted from the opening 15b of the puncture needle 15 is observed to detect the cutting of the optical fiber in the optical cable 70 and the optical fiber 14 in the puncture needle 15.

Figure 16:
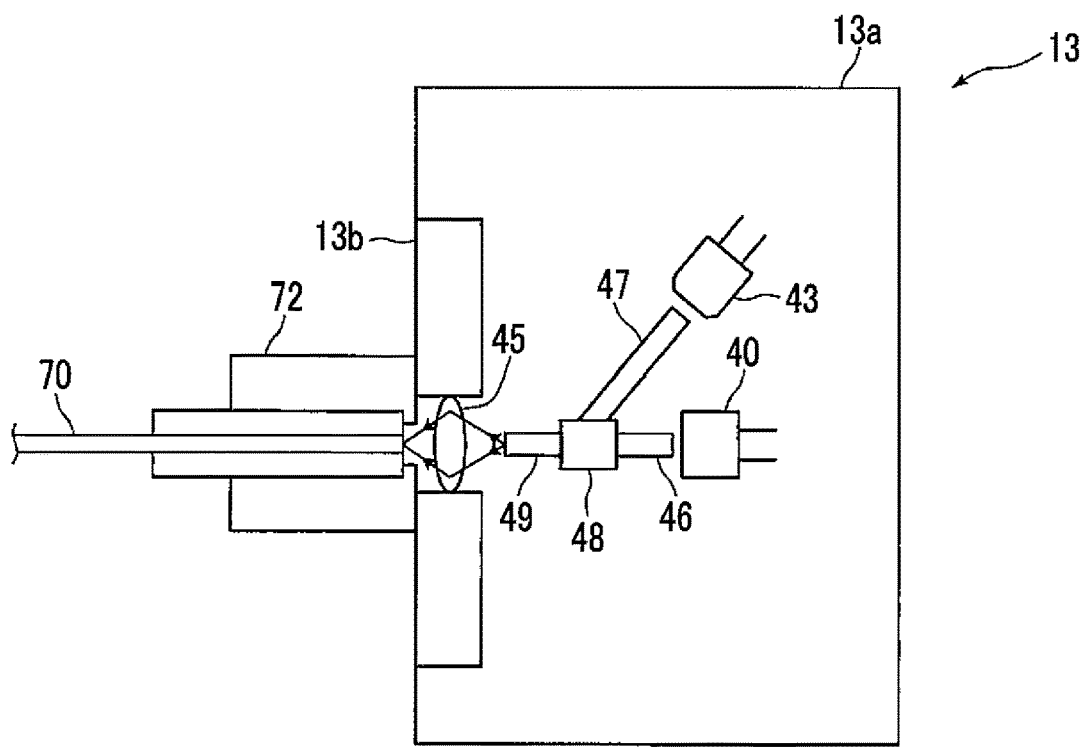
FIG. 16 is a diagram illustrating the internal configuration of still another example of the laser unit used to detect cutting.

The laser unit 13 for detecting cutting illustrated in FIG. 16 comprises an optical fiber 46 for laser light that guides pulsed laser light emitted from the pulsed laser light source 40, an optical fiber 47 for visible light that guides visible light emitted from the visible light source 43, a fiber combiner 48 that multiplexes the pulsed laser light guided by the optical fiber 46 for laser light and the visible light guided by the optical fiber 47 for visible light, and a multiplexing optical fiber 49 that guides the pulsed laser light and the visible light emitted from the fiber combiner 48 so as to be incident on the condensing lens 45. In the laser unit 13 illustrated in FIG. 16, the optical fiber 46 for laser light, the optical fiber 47 for visible light, the fiber combiner 48, the multiplexing optical fiber 49, and the condensing lens 45 correspond to the optical members according to the invention. In addition, condensing lenses may be provided between the visible light source 43 and the optical fiber 47 for visible light and between the pulsed laser light source 40 and the optical fiber 46 for laser light.

An operation after visible light is incident on the optical fiber in the optical cable 70 by the condensing lens 45 is the same as described above.

Figure 17:
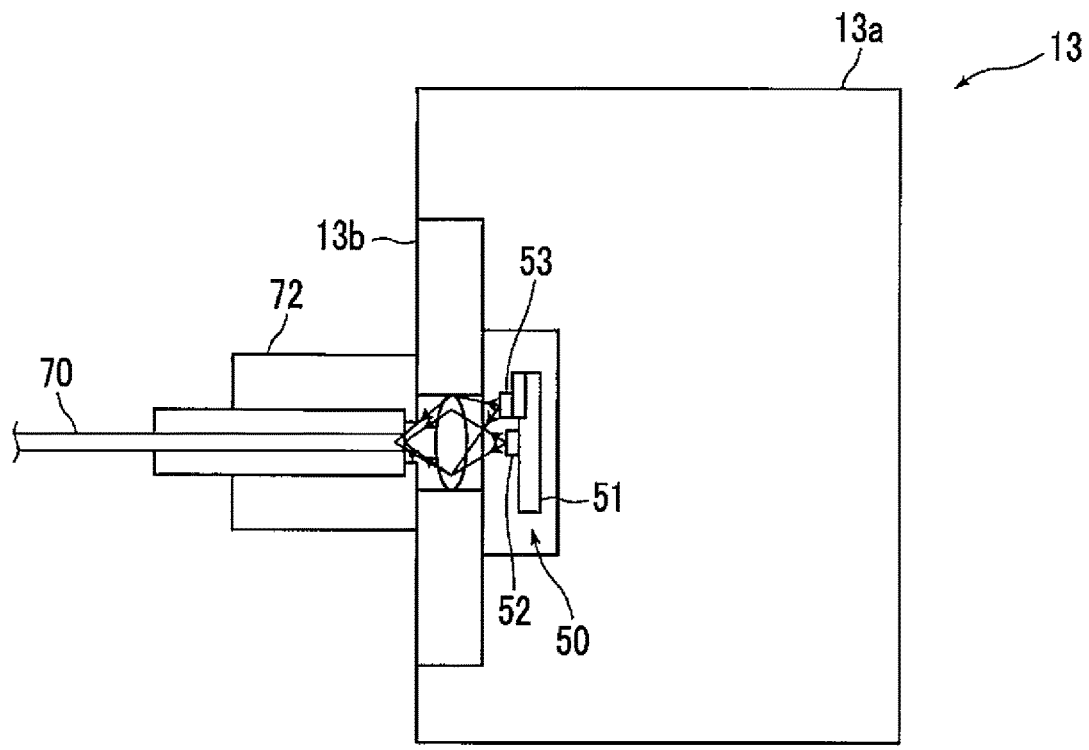
FIG. 17 is a diagram illustrating the internal configuration of yet another example of the laser unit used to detect cutting.

The laser unit 13 for detecting cutting illustrated in FIG. 17 comprises a pulsed laser diode (LD) chip 52 that emits pulsed laser light, a visible light emission diode (LED) chip 53 that emits visible light, and a driving control substrate 51 that is provided with the pulsed LD chip 52 and the visible LED chip 53 and drives the pulsed LD chip 52 and the visible LED chip 53.

The pulsed LD chip 52 is disposed such that the focal position of the pulsed laser light which has been emitted from the pulsed LD chip 52 and then condensed by the condensing lens 45 is located at the light incident end of the optical fiber in the optical cable 70. This configuration makes it possible to maximize propagation efficiency to the optical fiber in the optical cable 70. In contrast, the visible LED chip 53 is disposed such that the optical axis thereof deviates from the optical axis of the pulsed LD chip 52. The focal position of the visible light emitted from the visible LED chip 53 is not necessarily located at the light incident end of the optical fiber in the optical cable 70. However, the visible light emitted from the visible LED chip 53 may be incident on the optical fiber of the optical cable 70 to the extent that cutting can be detected. Therefore, there is no problem even in the above disposition. In addition, in the laser unit 13 illustrated in FIG. 17, the condensing lens 45 corresponds to the optical member according to the invention.

An operation after visible light is incident on the optical fiber in the optical cable 70 by the condensing lens 45 is the same as described above.

Figure 18:
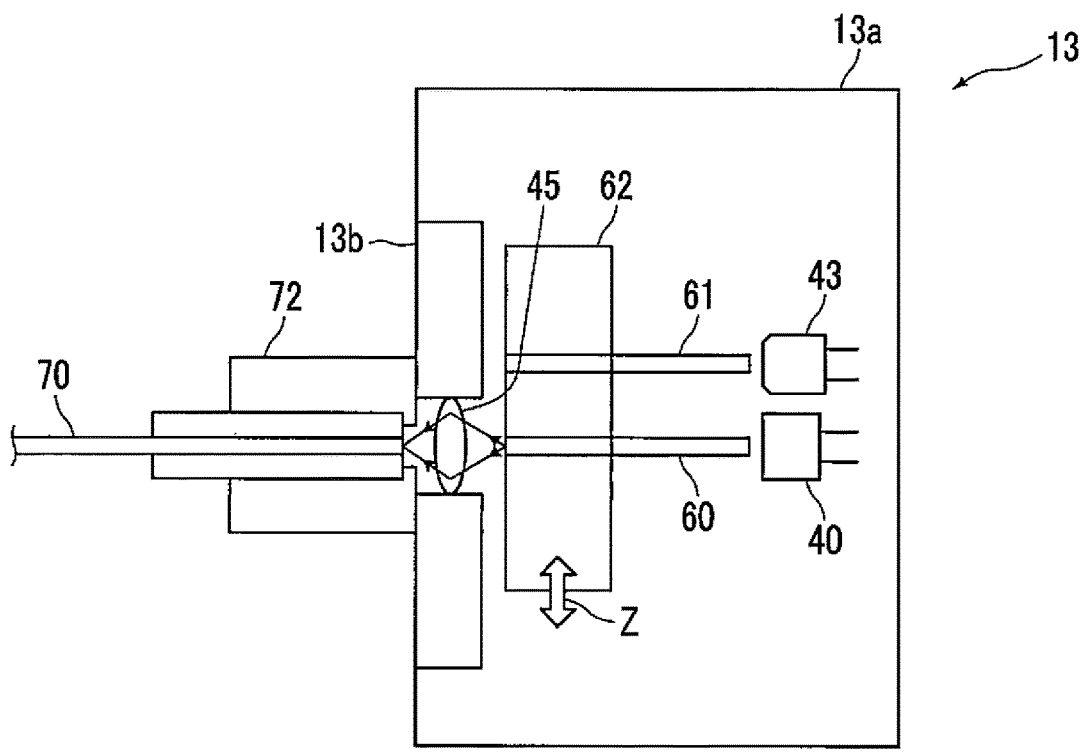
FIG. 18 is a diagram illustrating the internal configuration of still yet another example of the laser unit used to detect cutting.

The laser unit 13 for detecting cutting illustrated in FIG. 18 comprises a first optical fiber 60 that guides pulsed laser light emitted from the pulsed laser light source 40 and a second optical fiber 61 that guides visible light emitted from the visible light source 43. The first optical fiber 60 and the second optical fiber 61 are provided in a fiber switching unit 62. The fiber switching unit 62 is provided so as to reciprocate in the direction of an arrow Z illustrated in FIG. 18. The fiber switching unit 62 is moved in the Z direction to switch the position of a light emission end of the first optical fiber 60 and a light emission end of the second optical fiber 61 between a first position where light emitted from the first optical fiber 60 is incident on the condensing lens 45 and a second position where light emitted from the second optical fiber 61 is incident on the condensing lens 45. In the laser unit 13 illustrated in FIG. 18, the first optical fiber 60, the second optical fiber 61, and the condensing lens 45 correspond to the optical members according to the invention. It is assumed that the length and disposition of the first optical fiber 60 and the second optical fiber 61 are adjusted so as to be sufficiently flexibly curved with respect to the movement of the fiber switching unit 62. Alternatively, unlike this embodiment, the pulsed laser light source 40 and the visible light source 43 may be mounted on the fiber switching unit 62 and moved together.

An operation after visible light is incident on the optical fiber in the optical cable 70 by the condensing lens 45 is the same as described above.

In the above-described embodiments, the puncture needle 15 is considered as the insert. However, the invention is not limited thereto. The insert may be a radio-frequency ablation needle including an electrode that is used for radio-frequency ablation, a catheter that is inserted into a blood vessel, or a guide wire for a catheter that is inserted into a blood vessel.

The insert according to the invention is not limited to a needle, such as an injection needle, and may be a biopsy needle used for biopsy. That is, the insert may be a biopsy needle that is inserted into an inspection target of the living body and extracts the tissues of a biopsy site of the inspection target. In this case, photoacoustic waves may be generated from an extraction portion (intake port) for sucking and extracting the tissues of the biopsy site. In addition, the needle may be used as a guiding needle that is used for insertion into a deep part, such as a part under the skin or an organ inside the abdomen. The insert may also be used as a needle that passes through an endoscope and comes out of the forceps port.

The invention has been described above on the basis of the preferred embodiments. However, the insert and the photoacoustic measurement device according to the invention are not limited only to the above-described embodiments. Various modifications and changes of the configurations according to the above-described embodiments are also included in the scope of the invention. For example, a configuration the shape of the through-hole changes from a circular shape to a square shape, a configuration in which the shape of the through-hole changes from an elliptical shape to a rectangular shape, or a configuration in which the through-hole has a shape between the above-mentioned shapes is included in the scope of the invention. Alternatively, a configuration in which the position of the through-hole in the tip of the insertion is changed is also included in the scope of the invention.

What is claimed is:

1. An insert comprising:
    an insert main body which has an opening at a tip and is formed in a hollow shape and of which at least a tip portion of the tip is configured to be inserted into a subject;
    a light guide member that is provided in a hollow portion of the insert main body along a length direction of the insert main body; and
    a photoacoustic wave generation unit that is provided at a light emission end of the light guide member which is disposed on a tip side of the tip of the insert main body, absorbs light emitted from the light emission end, and generates photoacoustic waves,
    wherein the photoacoustic wave generation unit is made of a black resin, a material that transmits visible light, a material that transmits visible light and absorbs near-infrared light, or a material including a pigment that transmits visible light and absorbs near-infrared light and a photocurable resin,
    the insert main body is a guide wire for a catheter that is configured to be inserted into the subject,
    a through-hole is formed in a wall portion forming the hollow portion,
    the light emission end of the light guide member is positioned adjacent to the through-hole in a longitudinal direction of the insert main body, and
    the photoacoustic wave generation unit is fixed to the through-hole, thereby emitting photoacoustic waves which are generated by the photoacoustic wave generation unit from the opening at the tip and toward an exterior of the insert main body via the through hole,
    wherein the photoacoustic wave generation unit is provided to cover the light emission end of the light guide member,
    the through-hole is filled with the same material as that forming the photoacoustic wave generation unit integrally with the photoacoustic wave generation unit, and
    the photoacoustic wave generation unit and a tip portion of the light guide member are fixed to the wall portion.

2. The insert according to claim 1,
    wherein the through-hole has a shape in which the through-hole extends in the length direction of the insert main body rather than in a direction perpendicular to the length direction.

3. The insert according to claim 1,
    wherein the photoacoustic wave generation unit is fixed to the through-hole by a resin, and
    the through-hole is filled with the resin.

4. The insert according to claim 3,
    wherein the resin is a photocurable resin.

5. The insert according to claim 4,
    wherein the photocurable resin is a resin that is cured by visible light or ultraviolet light.

6. The insert according to claim 1,
    wherein the photoacoustic wave generation unit is made of the black resin.

7. The insert according to claim 1,
    wherein the photoacoustic wave generation unit is made of the material that transmits visible light.

8. The insert according to claim 7,
    wherein the material further absorbs near-infrared light.

9. The insert according to claim 8,
wherein the material further includes a photocurable resin.

10. The insert according to claim 1,
wherein the light guide member is an optical fiber.

11. A photoacoustic measurement device comprising:
the insert according to claim 1;
a light source unit that emits light which is absorbed by the photoacoustic wave generation unit of the insert; and
an acoustic wave detection unit that detects photoacoustic waves generated from the photoacoustic wave generation unit after at least a portion of the insert is inserted into the subject.

12. The photoacoustic measurement device according to claim 11,
wherein the photoacoustic wave generation unit is made of the material that transmits visible light, and
the light source unit comprises a first light source that emits the light which is absorbed by the photoacoustic wave generation unit and a second light source that emits the visible light.

13. The photoacoustic measurement device according to claim 12,
wherein the first light source emits near-infrared light.

14. The photoacoustic measurement device according to claim 12,
wherein the second light source emits the visible light from a surface of a housing of the light source unit to the outside of the housing.

15. The photoacoustic measurement device according to claim 12,
wherein the light source unit comprises optical members which include a multiplexing prism, a fiber combiner, a condensing lens that condenses both the light emitted from the first light source and the light emitted from the second light source, or a first optical fiber that guides the light emitted from the first light source and a second optical fiber that guides the light emitted from the second light source, and
the optical members make the light emitted from the first light source and the visible light emitted from the second light source incident on the light guide member of the insert.

16. The photoacoustic measurement device according to claim 15,
wherein the optical members include the multiplexing prism.

17. The photoacoustic measurement device according to claim 15,
wherein the optical members include the fiber combiner.

18. The photoacoustic measurement device according to claim 15,
wherein the optical members include the condensing lens.

19. The photoacoustic measurement device according to claim 15,
wherein the optical members include the first optical fiber and the second optical fiber, and
the photoacoustic measurement device further comprises a fiber switching unit that switches a position of a light emission end of the first optical fiber and a position of a light emission end of the second optical fiber between a first position where light emitted from the first optical fiber is incident on the light guide member and a second position where light emitted from the second optical fiber is incident on the light guide member.

* * * * *